(12) United States Patent
Saydam et al.

(10) Patent No.: US 11,946,935 B2
(45) Date of Patent: Apr. 2, 2024

(54) CIRCULATING TUMOR MARKERS FOR MENINGIOMAS

(71) Applicant: Regents of the University of Minnesota, Minneapolis, MN (US)

(72) Inventors: Nurten Saydam, Plymouth, MN (US); Okay Saydam, Plymouth, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 23 days.

(21) Appl. No.: 17/411,524

(22) Filed: Aug. 25, 2021

(65) Prior Publication Data

US 2022/0120755 A1    Apr. 21, 2022

Related U.S. Application Data

(60) Provisional application No. 63/070,010, filed on Aug. 25, 2020.

(51) Int. Cl.
*G01N 33/574* (2006.01)
*G01N 33/50* (2006.01)

(52) U.S. Cl.
CPC ... *G01N 33/57488* (2013.01); *G01N 33/5091* (2013.01); *G01N 2333/515* (2013.01); *G01N 2333/71* (2013.01); *G01N 2333/96466* (2013.01)

(58) Field of Classification Search
CPC ......... G01N 33/57488; G01N 33/5091; G01N 2333/515; G01N 2333/71; G01N 2333/96466
See application file for complete search history.

(56) References Cited

U.S. PATENT DOCUMENTS

| 2008/0050381 A1* | 2/2008 | Takeuchi ............... A61P 37/02 424/139.1 |
| 2013/0143232 A1* | 6/2013 | Liang ................ G01N 33/6893 435/23 |
| 2021/0085680 A1* | 3/2021 | Evans Raab ........... A61K 45/06 |

OTHER PUBLICATIONS

Erkan (Frontiers in Oncology 2019 vol. 9, article 1031; total 9 pages) (Year: 2019).*
Kumar (Oncology Reports 2006 15:1513-1516). (Year: 2006).*
Ciccarflli (J. Neurosurg Sci 2001 45:70-74) (Year: 2001).*
Konstantinidou (Apoptosis 2007 12:695-705) (Year: 2007).*

* cited by examiner

*Primary Examiner* — Changhwa J Cheu
(74) *Attorney, Agent, or Firm* — Schwegman Lundberg & Woessner, P.A.

(57) ABSTRACT

Methods and diagnostic compositions for detecting and monitoring meningiomas.

5 Claims, 9 Drawing Sheets

Specification includes a Sequence Listing.

CIRCULATING TUMOR MARKERS FOR MENINGIOMAS

CLAIM OF PRIORITY

This application claims the benefit of priority of U.S. Provisional Patent Application No. 63/070,010, filed on Aug. 25, 2020, the benefit of priority of which is claimed hereby, and which is incorporated by reference herein in its entirety.

BACKGROUND OF THE INVENTION

Meningiomas are primary central nervous system (CNS) tumors that originate from the arachnoid cells of the meninges. Recurrence occurs in higher grade meningiomas and a small subset of Grade I meningiomas with benign histology. Currently, there are no established circulating tumor markers which can be used for diagnostic and prognostic purposes in a non-invasive way for meningiomas.

SUMMARY OF THE INVENTION

Provided herein is a meningioma-specific protein signature in blood circulation of meningioma patients. Methods and diagnostic composition for detecting and monitoring meningiomas are disclosed herein.

One embodiment provides a method to detect a meningioma in a subject comprising obtaining a blood serum sample from a subject, measuring a level of amphiregulin, CCL24, CD69, prolactin, EGF, HB-EGF, caspase-3, VEGFD, TGF-α, E-Selectin, BAFF, IL-12, CCL9, and/or GH in said sample; and comparing the level of amphiregulin, CCL24, CD69, prolactin, EGF, HB-EGF, caspase-3, VEGF-D, TGF-α, E-Selectin, BAFF, IL-12, CCL9, and/or GH to a level of amphiregulin, CCL24, CD69, prolactin, EGF, HB-EGF, caspase-3, VEGF-D, TGF-α, E-Selectin, BAFF, IL-12, CCL9, and/or GH in a control serum sample, wherein an increase in levels of amphiregulin, CCL24, CD69, prolactin, EGF, HB-EGF, and/or caspase-3 and/or a decrease in levels of VEGF-D, TGF-α, E-Selectin, BAFF, IL-12, CCL9, and GH as compared to a control indicates a meningioma is present in said subject. In one embodiment, the level of caspase-3, amphiregulin and VEGF-D are detected. In another embodiment the measuring is achieved with an immunoassay selected from a group consisting of affinity capture assay, immunometric assay, heterogeneous chemiluminescence immunometric assay, homogeneous chemiluminescence immunometric assay, ELISA, western blotting, radioimmunoassay, magnetic immunoassay, real-time immune-quantitative PCR (iqPCR), SERS label free assay and combinations thereof. In one embodiment further comprising administering to the subject with a meningioma a treatment, wherein the treatment comprises surgery, radiation, immunotherapy, chemotherapy or a combination thereof.

Another embodiment provides a method of monitoring a meningioma in a subject, the method comprising: obtaining a first subject sample from a subject suffering from a meningioma, measuring a level of amphiregulin, CCL24, CD69, prolactin, EGF, HB-EGF, caspase-3, VEGFD, TGF-α, E-Selectin, BAFF, IL-12, CCL9, and/or GH in the first subject sample, comparing the level of CCL24, CD69, prolactin, EGF, HB-EGF, caspase-3, VEGFD, TGF-α, E-Selectin, BAFF, IL-12, CCL9, and/or GH obtained from the first subject sample to a level of CCL24, CD69, prolactin, EGF, HB-EGF, caspase-3, VEGFD, TGF-α, E-Selectin, BAFF, IL-12, CCL9, and/or GH in a control sample. In one embodiment, the method further comprises diagnosing the subject with a meningioma if the level of amphiregulin, CCL24, CD69, prolactin, EGF, HB-EGF, and/or caspase-3 is increased and/or the level of VEGF-D, TGF-α, E-Selectin, BAFF, IL-12, CCL9, and GH is decreased as compared to the level of CCL24, CD69, prolactin, EGF, HB-EGF, caspase-3, VEGFD, TGF-α, E-Selectin, BAFF, IL-12, CCL9, and/or GH in the control sample. Another embodiment further comprises obtaining a second subject sample a later point in time than the first sample; measuring a level of amphiregulin, CCL24, CD69, prolactin, EGF, HB-EGF, caspase-3, VEGFD, TGF-α, E-Selectin, BAFF, IL-12, CCL9, and/or GH in the second subject sample; and comparing the level of amphiregulin, CCL24, CD69, prolactin, EGF, HB-EGF, caspase-3, VEGFD, TGF-α, E-Selectin, BAFF, IL-12, CCL9, and/or GH in the first subject sample and the second subject sample, wherein a higher level of amphiregulin, CCL24, CD69, prolactin, EGF, HB-EGF, and/or caspase-3 and/or a lower level of VEGF-D, TGF-α, E-Selectin, BAFF, IL-12, CCL9, and GH in the second subject sample indicates the subject's meningioma is further progressing. Another embodiment further provides administering to the subject a treatment for meningioma; obtaining a second subject sample subsequent to commencement of the treatment; measuring a level of amphiregulin, CCL24, CD69, prolactin, EGF, HB-EGF, caspase-3, VEGFD, TGF-α, E-Selectin, BAFF, IL-12, CCL9, and/or GH in the second subject sample; and comparing the level of amphiregulin, CCL24, CD69, prolactin, EGF, HB-EGF, caspase-3, VEGFD, TGF-α, E-Selectin, BAFF, IL-12, CCL9, and/or GH in the first subject sample and the second subject sample, wherein a lower level of amphiregulin, CCL24, CD69, prolactin, EGF, HB-EGF, and/or caspase-3 and/or a higher level of VEGF-D, TGF-α, E-Selectin, BAFF, IL-12, CCL9, and GH in the second subject sample indicates the subject's responsiveness to the treatment regimen. In one embodiment, the level of caspase-3, amphiregulin and VEGF-D are detected. In one embodiment, the treatment comprises surgery, radiation, immunotherapy, chemotherapy or a combination thereof. In one embodiment, the measuring is achieved with an immunoassay selected from a group consisting of affinity capture assay, immunometric assay, heterogeneous chemiluminescence immunometric assay, homogeneous chemiluminescence immunometric assay, ELISA, western blotting, radioimmunoassay, magnetic immunoassay, real-time immune-quantitative PCR (iqPCR), SERS label free assay and combinations thereof.

One embodiment provides a solid support having one or more of amphiregulin, CCL24, CD69, prolactin, EGF, HB-EGF, caspase-3, VEGFD, TGF-α, E-Selectin, BAFF, IL-12, CCL9, and/or GH attached thereto, wherein the solid support is a chip, glass slide, a microtiter plate, a bead or resin. In one embodiment, caspase-3, amphiregulin and VEGF-D are attached to the sold support.

DETAILED DESCRIPTION OF THE INVENTION

Figure 1A:
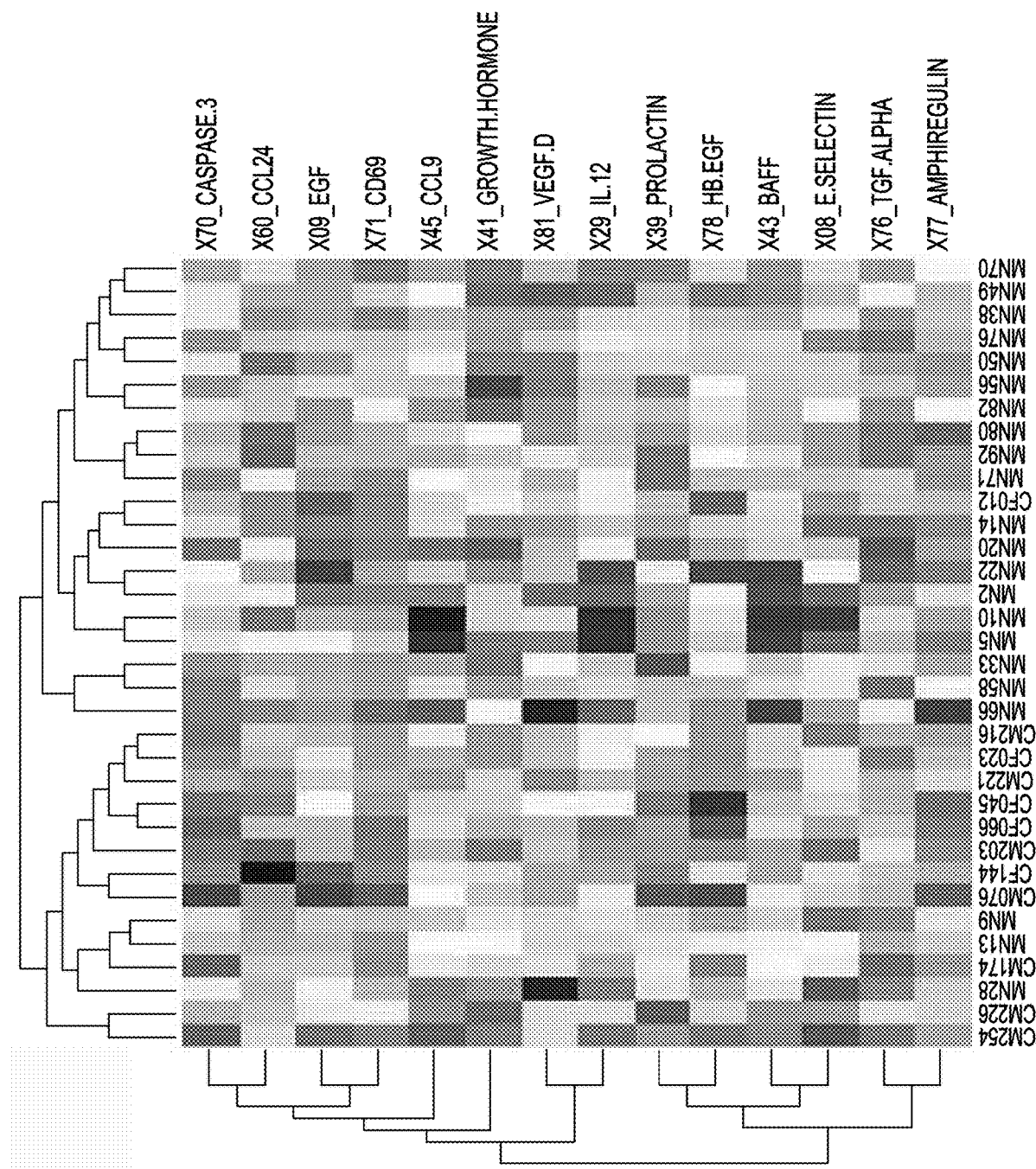
FIGS. 1A-1C-7 Differentially expressed proteins between meningioma patients and control subjects. ROTS algorithm was used to identify differentially expressed proteins between Grade I meningioma patients and healthy control subjects (A). Heatmap visualization of differentially expressed proteins (B,C). Comparison of protein levels across tumor grades ($*p<0.05$, $p<0.01$, $*p<0.001$, $****p<0.0001$).

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It will be understood that various changes may be made in the function and arrangement of elements without departing from the spirit and scope of the disclosure as set forth in the appended claims.

Specific details are given in the following description to provide a thorough understanding of the embodiments. However, it will be understood by one of ordinary skill in the art that the embodiments may be practiced without these specific details. For example, systems, processes, and other elements in the instant disclosure may be shown as components in block diagram form in order not to obscure the embodiments in unnecessary detail. In other instances, well-known processes, structures, and techniques may be shown without unnecessary detail in order to avoid obscuring the embodiments.

Definitions

In describing and claiming the invention, the following terminology will be used in accordance with the definitions set forth below. Unless defined otherwise, all technical and scientific terms used herein have the same meaning as commonly understood by one of ordinary skill in the art to which this invention belongs. Any methods and materials similar or equivalent to those described herein can be used in the practice or testing of the present invention. Specific and preferred values listed below for radicals, substituents, and ranges are for illustration only; they do not exclude other defined values or other values within defined ranges for the radicals and substituents.

As used in this specification and the appended claims, the singular forms "a," "an," and "the" include plural references unless the context clearly dictates otherwise. By way of example, "an element" means one element or more than one element. Similarly, references to "the method" includes one or more methods, and/or steps of the type described herein and/or which will become apparent to those persons skilled in the art upon reading this disclosure and so forth.

As used herein, the term "about" means acceptable variations within 20%, such as within 10% or within 5% of the stated value.

Meningioma is the most common type of primary brain tumor, accounting for approximately 30 percent of all brain tumors. It originates in the meninges, the outer three layers of protective tissue located between the skull and the brain. The severity of a meningioma is determined by its grade (classification) and location. Meningioma grading (I to III) is based on the appearance of the tumor cells under a microscope. Grade I is the most common type of meningioma and is considered benign. Grade III is the most aggressive form and is considered malignant. The following guide outlines the meningioma grading system: Grade I (benign). This noncancerous type of brain tumor grows slowly and has distinct borders. Approximately 78 percent to 81 percent of meningiomas are benign (noncancerous). Grade II (atypical): Approximately 15 percent to-20 percent of meningiomas are atypical, which means that the tumor cells do not appear typical or normal. Atypical meningiomas are neither malignant (cancerous) nor benign but may become malignant at some point. Grade II meningiomas also tend to recur and grow faster. Grade III (malignant or anaplastic): This aggressive type of brain tumor tends to invade the parts of the brain that are closest to the tumor. Approximately 1 percent to 4 percent of meningiomas are grade III (cancerous).

As used herein the terms "biomarker" or "marker" generally refer to a protein, nucleic acid molecule, clinical indicator, or other analyte that is associated with a disease. In one embodiment, a marker of meningioma is differentially present in a biological sample obtained from a subject having or at risk of developing meningioma relative to a reference. A marker is differentially present if the level of the biomarker present in the sample is different (e.g. statistically different from the level present in a control sample. A control sample level may be, for example, the level present in a sample obtained from a healthy control subject or the level obtained from the subject at an earlier timepoint, i.e., prior to treatment. Common tests for statistical significance include, among others, t-test, ANOVA, Kruskal-Wallis, Wilcoxon, Mann-Whitney and odds ratio. Biomarkers, alone or in combination, provide measures of relative likelihood that a subject belongs to a phenotypic status of interest. The differential presence of a marker of the invention in a subject sample can be useful in characterizing the subject as having or at risk of developing meningioma, for determining the prognosis of the subject, for evaluating therapeutic efficacy, or for selecting a treatment regimen (e.g., selecting that the subject be evaluated and/or treated by a surgeon that specializes in oncology).

As used herein, "caspase-3" refers to a caspase protein that interacts with caspase-8 and caspase-9. It is encoded by the CASP3 gene. CASP3 orthologs have been identified in numerous mammals for which complete genome data are available. The CASP3 protein is a member of the cysteineaspartic acid protease (caspase) family. Sequential activation of caspases plays a role in the execution-phase of cell apoptosis. Caspases exist as inactive proenzymes that undergo proteolytic processing at conserved aspartic residues to produce two subunits, large and small, that dimerize to form the active enzyme. This protein cleaves and activates caspases 6 and 7; and the protein itself is processed and activated by caspases 8, 9, and 10. (Human mRNA NM_004346 and NM_032991; human protein NP_004337; NP_116786: NP_001341706; NP_001341708 and NP_001341709)

As used herein, "amphiregulin," also known as AREG, is a transmembrane glycoprotein with 252 amino acids and it is encoded by the AREG gene in human. The protein encoded by this gene is a member of the epidermal growth factor (EGF) family. It is an autocrine growth factor as well as a mitogen for astrocytes, Schwann cells, and fibroblasts. It is ligand for epidermal growth factor (EGF) and it is related to transforming growth factor alpha (TGF-alpha). This protein interacts with the epidermal growth factor receptor (EGFR) to promote the growth of normal epithelial cells. (Human mRNA NM_001657 and human protein NP_001648.)

As used herein, "VEGF-D" refers to a vascular endothelial growth factor that in humans is encoded by the FIGF gene. The protein encoded by this gene is a member of the platelet-derived growth factor/vascular endothelial growth factor (PDGF/VEGF) family and is active in angiogenesis, lymphangiogenesis, and endothelial cell growth. This secreted protein undergoes a complex proteolytic maturation, generating multiple processed forms that bind and activate VEGFR-2 and VEGFR-3 receptors. The structure and function of this protein is similar to those of vascular endothelial growth factor C. (Human mRNA NM_004469 and human protein NP_004460.)

As used herein, "CCL24" refers to Chemokine (C-C motif) ligand 24 (CCL24) also known as myeloid progenitor inhibitory factor 2 (MPIF-2) or eosinophil chemotactic protein 2 (eotaxin-2) and is a protein that in humans is encoded by the CCL24 gene. CCL24 is a small cytokine belonging to the CC chemokine family. CCL24 interacts with chemokine receptor CCR3 to induce chemotaxis in eosinophils. (NM_002991)

As used herein, "CD69" refers to Cluster of Differentiation 69 and is a human transmembrane C-Type lectin protein encoded by the CD69 gene. It is an early activation marker that is expressed in hematopoietic stem cells, T cells, and many other cell types in the immune system. The activation of T lymphocytes and Natural Killer (NK) Cells, both in vivo and in vitro, induces expression of CD69. This molecule, which appears to be the earliest inducible cell surface glycoprotein acquired during lymphoid activation, is involved in lymphocyte proliferation and functions as a signal-transmitting receptor in lymphocytes, including natural killer (NK) cells, and platelets. (Human mRNA NM_001781 and human protein NP_001772.)

As used herein, "prolactin" (encoded by the PRL gene), also known as lactotropin, is a protein hormone that plays a role in enabling mammals (and birds), usually females, to produce milk. Prolactin is secreted from the pituitary gland in response to eating, mating, estrogen treatment, ovulation and nursing. Prolactin plays a role in metabolism, regulation of the immune system and pancreatic development.

As used herein, "EGF" refers Epidermal growth factor (EGF) which is a protein that stimulates cell growth and differentiation by binding to its receptor, EGFR. Human EGF is 6-kDa and has 53 amino acid residues and three intramolecular disulfide bonds. (Human mRNA NM_001178130, NM_001178131, NM_001963, NM_001357021 and human protein NP_001171601, NP_001171602, NP_001954, NP_001343950.)

As used herein, "HB-EGF" refers to Heparin-binding EGF-like growth factor (HB-EGF) which is a member of the EGF family of proteins that in humans is encoded by the HBEGF gene. HB-EGF-like growth factor is synthesized as a membrane-anchored mitogenic and chemotactic glycoprotein. An epidermal growth factor produced by monocytes and macrophages, due to an affinity for heparin is termed HB-EGF. It has been shown to play a role in wound healing, cardiac hypertrophy, and heart development and function. (Human mRNA NM_001945 and human protein NP_001936.)

As used herein, "TGF-α" refers to Transforming growth factor alpha (TGF-α) which is a protein that in humans is encoded by the TGFA gene. As a member of the epidermal growth factor (EGF) family, TGF-α is a mitogenic polypeptide. The protein becomes activated when binding to receptors capable of protein kinase activity for cellular signaling. TGF-α is a transforming growth factor that is a ligand for the epidermal growth factor receptor, which activates a signaling pathway for cell proliferation, differentiation and development. This protein may act as either a transmembrane-bound ligand or a soluble ligand. (Human mRNA NM_001099691, NM_001308158, NM_001308159, NM_003236 and human protein NP_001093161, NP_001295087, NP_001295088, NP_003227.)

As used herein, "E-Selectin," also known as CD62 antigen-like family member E (CD62E), endothelial-leukocyte adhesion molecule 1 (ELAM-1), or leukocyte-endothelial cell adhesion molecule 2 (LECAM2), is a selectin cell adhesion molecule expressed on endothelial cells activated by cytokines. Like other selectins, it plays a part in inflammation. In humans, E-selectin is encoded by the SELE gene. (Human mRNA NM_000450 and human protein NP_000441.)

As used herein, "IL-12" refers to Interleukin 12 which is an interleukin that is naturally produced by dendritic cells, macrophages, neutrophils, and human B-lymphoblastoid cells (NC-37) in response to antigenic stimulation. IL-12 belongs to the family of interleukin-12. IL-12 family is unique in comprising the only heterodimeric cytokines, which includes IL-12, IL-23, IL-27 and IL-35. (NM_000882.)

As used herein, "BAFF" refers to B-cell activating factor, also known as tumor necrosis factor ligand superfamily member 13B and is a protein that in humans is encoded by the TNFSF13B gene. BAFF is also known as B Lymphocyte Stimulator (BLyS) and TNF- and APOL-related leukocyte expressed ligand (TALL-1) and the Dendritic cell-derived TNF-like molecule (CD257 antigen; cluster of differentiation 257). (Human mRNA NM_001145645 and NM_006573 and human protein NP_001139117 and NP_006564.)

As used herein, "CCL9" refers to Chemokine (C-C motif) ligand 9 (CCL9) which is a small cytokine belonging to the CC chemokine family. It is also called macrophage inflammatory protein-1 gamma (MIP-1γ), macrophage inflammatory protein-related protein-2 (MRP-2) and CCF18. It is secreted by follicle-associated epithelium (FAE) such as that found around Peyer's patches, and attracts dendritic cells that possess the cell surface molecule CD11b and the chemokine receptor CCR1. CCL9 can activate osteoclasts through its receptor CCR1 (the most abundant chemokine receptor found on osteoclasts) suggesting a role for CCL9 in bone resorption. CCL9 is constitutively expressed in macrophages and myeloid cells. (Human mRNA NM_011338 and human protein NP_035468.)

As used herein, "GH" refers to Growth hormone or somatotropin, also known as human growth hormones (hGH or HGH) in its human form, is a peptide hormone that stimulates growth, cell reproduction, and cell regeneration in humans and other animals. GH also stimulates production of IGF-1 and increases the concentration of glucose and free fatty acids. It is a type of mitogen which is specific only to the receptors on certain types of cells. GH is a 191-amino acid, single-chain polypeptide that is synthesized, stored and secreted by somatotropic cells within the lateral wings of the anterior pituitary gland. (NM_022562 and NM_002059.)

The term "isolated" refers to a factor(s), cell or cells which are not associated with one or more factors, cells or one or more cellular components that are associated with the factor(s), cell or cells in vivo.

"Cells" include cells from, or the "subject," "patient," is, a vertebrate, such as a mammal, including a human. Mammals include, but are not limited to, humans, farm animals, sport animals and companion animals. Included in the term "animal" is dog, cat, fish, gerbil, guinea pig, hamster, horse, rabbit, swine, mouse, monkey (e.g., ape, gorilla, chimpanzee, or orangutan), rat, sheep, goat, cow and bird.

The screen/assay for markers can be done at any age, including for example, a screen at birth or from 0-5 years of age, 5-10 years of age, 10-15 years of age, 15-20 years of age, 20-25 years of age, 25-30 years of age, 30-35 years of age, 35-40 years of age, 40-45 years of age, 45-50 years of age, 50-55 years of age, 55-60 years of age, 60-65 years of age, 65-70 years of age, 70-75 years of age, 75-80 years of age, 85-90 years of age, 90-95 years of age, 95-100 years of age and so on.

The terms "treat," "treating," and "treatment," as used herein, refer to therapeutic or preventative measures such as those described herein. The methods of "treatment" employ administration to a patient of a treatment regimen in order to prevent, cure, delay, reduce the severity of, or ameliorate one or more symptoms of the disease or disorder or recurring disease or disorder, or in order to prolong the survival of a patient beyond that expected in the absence of such treatment. Treatment for a meningioma includes active surveillance (during active surveillance, the tumor is monitored, and treatment would begin if it started causing any symptoms or problems or showed an alteration in the level of serum markers as described herein), surgery, radiation (such as external-beam radiation, including conventional radiation therapy, intensity modulated radiation therapy (IMRT), 3-dimensional conformal radiation therapy; stereotactic radiosurgery, fractionated stereotactic radiation therapy or proton radiation therapy), immunotherapy and chemotherapy.

The term "effective amount," as used herein, refers to that amount of an agent, which is sufficient to effect treatment, prognosis or diagnosis of meningioma, when administered to a patient. A therapeutically effective amount will vary depending upon the patient and disease condition being treated, the weight and age of the patient, the severity of the disease condition, the manner of administration and the like, which can readily be determined by one of ordinary skill in the art.

Other terms used in the fields of recombinant nucleic acid technology, microbiology, immunology, antibody engineering and molecular and cell biology as used herein will be generally understood by one of ordinary skill in the applicable arts. For example, conventional techniques may be used for preparing recombinant DNA, performing oligonucleotide synthesis, and practicing tissue culture and transformation (e.g., electroporation, transfection or lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See, e.g., Sambrook et al., 2001, Molecular Cloning: A Laboratory Manual, 3rd ed., Cold Spring Harbor Laboratory Press, Cold Spring Harbor, N.Y., which is incorporated herein by reference for any purpose. Unless specific definitions are provided, the nomenclature utilized in connection with, and the laboratory procedures and techniques of, analytical chemistry, synthetic organic chemistry, and medicinal and pharmaceutical chemistry described herein are those well-known and commonly used in the art. Standard techniques may be used for chemical syntheses, chemical analyses, pharmaceutical preparation, formulation, and delivery, and treatment of patients.

By "biologic sample" is meant any tissue, cell, fluid (such as blood or serum), or other material derived from an organism.

As used herein, the terms "determining", "assessing", "assaying", "measuring" and "detecting" refer to both quantitative and qualitative determinations, and as such, the term "determining" is used interchangeably herein with "assaying," "measuring," and the like. Where a quantitative determination is intended, the phrase "determining an amount" of an analyte and the like is used. Where a qualitative and/or quantitative determination is intended, the phrase "determining a level" of an analyte or "detecting" an analyte is used.

By "reference" is meant a standard of comparison. For example, the marker level(s) present in a patient sample may be compared to the level of the marker in a corresponding healthy cell or tissue or in a diseased cell or tissue (e.g., a cell or tissue derived from a subject having meningioma). In particular embodiments, amphiregulin, CCL24, CD69, prolactin, EGF, HB-EGF, caspase-3, VEGFD, TGF-α, E-Selectin, BAFF, IL-12, CCL9, and/or GH polypeptide level present in a patient sample may be compared to the level of said polypeptide present in a corresponding sample obtained at an earlier time point (i.e., prior to treatment), to a healthy cell or tissue or a neoplastic cell or tissue that lacks a propensity at a different grade. As used herein, the term "sample" includes a biologic sample such as any tissue, cell, fluid, or other material derived from an organism.

By "specifically binds" is meant a compound (e.g., antibody) that recognizes and binds a molecule (e.g., polypeptide), but which does not substantially recognize and bind other molecules in a sample, for example, a biological sample.

As used herein the term "comprising," "having" and "including" and the like are used in reference to compositions, methods, and respective component(s) thereof, that are present in a given embodiment, yet open to the inclusion of one more or more unspecified elements. The term "including" is used herein to mean, and is used interchangeably with, the phrase "including but not limited to."

As used herein the term "consisting essentially of" refers to those elements required for a given embodiment. The term permits the presence of additional elements that do not materially affect the basic and novel or functional characteristic(s) of that embodiment of the invention. The term "consisting of" refers to compositions, methods, and respective components thereof as described herein, which are exclusive of any element not recited in that description of the embodiment.

Amphiregulin, CCL24, CD69, Prolactin, EGF, HB-EGF, Caspase-3, VEGFD, TGF-α, E-Selectin, BAFF, IL-12, CCL9, and/or GH Biomarkers and Use Thereof Meningiomas are primary central nervous system (CNS) tumors that originate from the arachnoid cells of the meninges. Recurrence occurs in higher grade meningiomas and a small subset of Grade I meningiomas with benign histology. Until now, there are no circulating tumor markers known which can be used for diagnostic and prognostic purposes in a non-invasive way for meningiomas.

Generally, diagnose or monitor status of tumor growth in the clinic, MRI or PET is used. MRI is only able to detect tumor when it gets to the certain size. However, tumor markers can be used any time to determine the presence or the status of a tumor and are much more sensitive than MRI or PET, and less the test is less expensive. One microL of serum is enough to detect the markers disclosed herein and can be used in any lab in the world, such as where MRI facility is not available.

Provided herein is a serum signature in which amphiregulin, CCL24, CD69, prolactin, EGF, HB-EGF, caspase-3, VEGFD, TGF-α, E-Selectin, BAFF, IL-12, CCL9, and/or GH, such as caspase3, amphiregulin and VEGF-D, can be used to detect, diagnose and monitor the status of tumor growth and transition stages from grade I to II and III (and over the course of treatment/response to treatment of the meningioma). Expression of amphiregulin and Caspase3 are increased in all grades of meningiomas, either at the transcriptional or protein level. While the gene expression of VEGF-D is lower in Grade I meningioma. Amphiregulin, Caspase 3 and VEGF-D can be used as a commercialized one-cancer panel array, including as a multiplex ELISA, for meningiomas.

Detection of Amphiregulin, CCL24, CD69, Prolactin, EGF, HB-EGF, Caspase-3, VEGFD, TGF-α, E-Selectin, BAFF, IL-12, CCL9, and/or GH The level of amphiregulin, CCL24, CD69, prolactin, EGF, HB-EGF, caspase-3, VEGFD, TGF-α, E-Selectin, BAFF, IL-12, CCL9, and/or GH biomarkers can be detected in a biological sample of the subject (e.g., tissue, fluid). Suitable samples include, but are not limited to, blood, blood serum, plasma, and/or a cell isolated from a patient sample.

Amphiregulin, CCL24, CD69, prolactin, EGF, HB-EGF, caspase-3, VEGFD, TGF-α, E-Selectin, BAFF, IL-12, CCL9, and/or GH can be detected by any suitable method. The methods described herein can be used individually or in combination for a more accurate detection of the biomarkers (e.g., biochip in combination with mass spectrometry, immunoassay in combination with mass spectrometry, and the like).

Detection methods that can be employed for detection of amphiregulin, CCL24, CD69, prolactin, EGF, HB-EGF, caspase-3, VEGFD, TGF-α, E-Selectin, BAFF, IL-12, CCL9, and/or GH include, but are not limited to, optical methods, electrochemical methods (voltammetry and amperometry techniques), atomic force microscopy, and radio frequency methods, e.g., multipolar resonance spectroscopy.

In some embodiments, the levels of amphiregulin, CCL24, CD69, prolactin, EGF, HB-EGF, caspase-3, VEGFD, TGF-α, E-Selectin, BAFF, IL-12, CCL9, and/or GH can be measured by immunoassay. Immunoassay typically utilizes an antibody (or other agent that specifically binds the marker) to detect the presence or level of a biomarker in a sample. Antibodies can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies by methods well known in the art. Further, one can use a commercial antibody.

Suitable immunoassay detection methods include, for example, Western blot, sandwich immunoassays including ELISA and other enzyme immunoassays, fluorescence-based immunoassays, and chemiluminescence. Nephelometry is an assay done in liquid phase, in which antibodies are in solution. Binding of the antigen to the antibody results in changes in absorbance, which is measured. Other forms of immunoassay include magnetic immunoassay, radioimmunoassay, and real-time immunoquantitative PCR (iqPCR).

In some embodiments, the level of amphiregulin, CCL24, CD69, prolactin, EGF, HB-EGF, caspase-3, VEGFD, TGF-α, E-Selectin, BAFF, IL-12, CCL9, and/or GH can be detected by mass spectrometry (MS). Mass spectrometry is a well-known tool for analyzing chemical compounds that employs a mass spectrometer to detect gas phase ions. Mass spectrometers are well known in the art and include, but are not limited to, time-of-flight, magnetic sector, quadrupole filter, ion trap, ion cyclotron resonance, electrostatic sector analyzer and hybrids of these. The method may be performed in an automated (Villanueva, et al., Nature Protocols (2006) 1(2):880-891) or semi-automated format. This can be accomplished, for example with the mass spectrometer operably linked to a liquid chromatography device (LC-MS/MS or LC-MS) or gas chromatography device (GC-MS or GC-MS/MS).

In some embodiments, amphiregulin, CCL24, CD69, prolactin, EGF, HB-EGF, caspase-3, VEGFD, TGF-α, E-Selectin, BAFF, IL-12, CCL9, and/or GH will be detected, quantitate and/or monitored by ELISA. In some embodiments, amphiregulin, CCL24, CD69, prolactin, EGF, HB-EGF, caspase-3, VEGFD, TGF-α, E-Selectin, BAFF, IL-12, CCL9, and/or GH can be determined by an LC-MS method or via an electrochemical detection method using microelectrodes (either static-cell or flow-cell electrodes). In some embodiments, the detection/monitoring may comprise colorimetric, chemiluminescence or fluorometric assays. However, as noted above, other known methods or techniques can be used to detect the level of amphiregulin, CCL24, CD69, prolactin, EGF, HB-EGF, caspase-3, VEGFD, TGF-α, E-Selectin, BAFF, IL-12, CCL9, and/or GH.

Antibodies for ELISA

Antibodies against amphiregulin, CCL24, CD69, prolactin, EGF, HB-EGF, caspase-3, VEGFD, TGF-α, E-Selectin, BAFF, IL-12, CCL9, and/or GH can be purchased and/or prepared. Various methods are available to one of skill in the art that can be used to prepare amphiregulin, CCL24, CD69, prolactin, EGF, HB-EGF, caspase-3, VEGFD, TGF-α, E-Selectin, BAFF, IL-12, CCL9, and/or GH antibodies.

An "antibody," as used herein is a protein consisting of one or more polypeptides comprising binding domains substantially encoded by immunoglobulin genes or fragments of immunoglobulin genes, wherein the protein immune-specifically binds to an antigen. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin structural unit comprises a tetramer that is composed of two identical pairs of polypeptide chains, each pair having one "light" (about 25 kD) and one "heavy" chain (about 50-70 kD). "VL" and VH" refer to these light and heavy chains respectively.

Antibodies include intact immunoglobulins as well as antigen-binding fragments thereof, which may be produced by digestion with various peptidases, or synthesized de novo either chemically or using recombinant DNA expression technology. Such fragments include, for example, F(ab)2 dimers and Fab monomers. Useful antibodies include single chain antibodies (antibodies that exist as a single polypeptide chain), e.g., single chain Fv antibodies (scFv) in which a VH and a VL chain are joined together (directly or through a peptide linker) to form a continuous polypeptide.

Antibodies also include variants, chimeric antibodies and humanized antibodies. The term "antibody variant" or "variant" as used herein refers to an antibody with single or multiple mutations in the heavy chains and/or light chains. In some embodiments, the mutations exist in the variable region. In some embodiments, the mutations exist in the constant region. "Chimeric antibodies" refers to those antibodies wherein one portion of each of the amino acid sequences of heavy and light chains is homologous to corresponding sequences in antibodies derived from a particular species or belonging to a particular class, while the remaining segment of the chains is homologous to corresponding sequences in another. Typically, in these chimeric antibodies, the variable region of both light and heavy chains mimics the variable regions of antibodies derived from one species of mammals, while the constant portions are homologous to the sequences in antibodies derived from another. One clear advantage to such chimeric forms is that, for example, the variable regions can conveniently be derived from presently known sources using readily available hybridomas or B cells from non-human host organisms in combination with constant regions derived from, for example, human cell preparations. While the variable region has the advantage of ease of preparation, and the specificity is not affected by its source, the constant region being human, is less likely to elicit an immune response from a human subject when the antibodies are injected than would the constant region from a non-human source. However, the definition is not limited to this particular example. "Humanized" antibodies refer to a molecule having an antigen-binding site that is substantially derived from an immunoglobulin from a non-human species and the remaining immunoglobulin structure of the molecule based upon the structure and/or sequence of a human immunoglobulin. The antigen-binding site may comprise either complete variable domains fused onto constant domains or only the complementarity determining regions (CDRs) grafted onto appropriate framework regions in the variable domains. Antigen binding sites may be wild type or modified by one or more amino acid substitutions, e.g., modified to resemble human immunoglobulin more closely. Some forms of humanized antibodies preserve all CDR sequences (for example, a humanized mouse antibody which contains all six CDRs from the mouse antibodies). Other forms of humanized antibodies have one or more CDRs (one, two, three, four, five, or six) which are altered with respect to the original antibody, which are also termed one or more CDRs "derived from" one or more CDRs.

Compositions and Kits

Compositions and kits for detecting amphiregulin, CCL24, CD69, prolactin, EGF, HB-EGF, caspase-3, VEGFD, TGF-α, E-Selectin, BAFF, IL-12, CCL9, and/or GH and thus, diagnosing or monitoring meningioma are also provided. In some embodiments, a composition is provided that includes an agent that recognizes amphiregulin, CCL24, CD69, prolactin, EGF, HB-EGF, caspase-3, VEGFD, TGF-α, E-Selectin, BAFF, IL-12, CCL9, and/or GH. In some embodiments, a kit is provided that includes an agent that recognizes amphiregulin, CCL24, CD69, prolactin, EGF, HB-EGF, caspase-3, VEGFD, TGF-α, E-Selectin, BAFF, IL-12, CCL9, and/or G. In some embodiments, the compositions and kits of the present disclosure can include one or more amphiregulin, CCL24, CD69, prolactin, EGF, HB-EGF, caspase-3, VEGFD, TGF-α, E-Selectin, BAFF, IL-12, CCL9, and/or GH antibodies, or antigen binding fragment thereof, for use in connection with an immunoassay such as immunohistochemistry or ELISA or Western blot.

Alternatively, the kit can include specific primers and/or probes for use in connection with qRT-PCR (e.g., using primers of 10-30 bp designed to target amphiregulin, CCL24, CD69, prolactin, EGF, HB-EGF, caspase-3, VEGFD, TGF-α, E-Selectin, BAFF, IL-12, CCL9, and/or GH) or Northern blot (e.g., using probes of 30-300 bp designed to target amphiregulin, CCL24, CD69, prolactin, EGF, HB-EGF, caspase-3, VEGFD, TGF-α, E-Selectin, BAFF, IL-12, CCL9, and/or GH). The kit can also include a microarray for detecting amphiregulin, CCL24, CD69, prolactin, EGF, HB-EGF, caspase-3, VEGFD, TGF-α, E-Selectin, BAFF, IL-12, CCL9, and/or GH mRNA or protein level.

In some embodiments, the kit comprises a solid support, such as a chip, a microtiter plate or a bead or resin having capture reagents attached thereon. Any method available to an art worker to attached capture agents (e.g., the biomarkers disclosed herein) can be used.

The kit can also comprise a washing solution or instructions for making a washing solution, in which the combination of the capture reagent and the washing solution allows capture of the biomarker or biomarkers on the solid support for subsequent detection by, e.g., mass spectrometry or ELISA. The kit may include more than type of adsorbent, each present on a different solid support.

In a further embodiment, such a kit can comprise instructions for use in any of the methods described herein. In embodiments, the instructions provide suitable operational parameters in the form of a label or separate insert. For example, the instructions may inform a consumer about how to collect the sample, how to wash the probe or the particular biomarkers to be detected.

A control sample can additionally be included in the kit, wherein a difference in the test sample compared to the control sample can indicates a status of meningioma. The change can be more than about 10%, more than about 20%, more than about 30%, more than about 50%, more than about 60%, more than about 80%, more than about 100%, or more, or any number therebetween. The control sample may be indicative of a healthy individual, or an individual having meningioma of one or more grades and severities.

The compositions and methods of the present disclosure are described in the following Examples, which are set forth to aid in the understanding of the disclosure and should not be construed to limit in any way the scope of the disclosure as defined in the claims which follow thereafter. The following examples are put forth so as to provide those of ordinary skill in the art with a disclosure and description of how to make and use the embodiments of the present disclosure and are not intended to limit the scope of what the inventors regard as their invention nor are they intended to represent that the experiments below are all or the only experiments performed.

EXAMPLES

Circulating Tumor Biomarkers in Meningiomas
Introduction

Meningiomas account for 53.1% of all non-malignant brain and other CNS tumors (1). The majority of meningiomas with documented WHO grade is Grade I (80.6%) (1). These benign tumors can remain dormant without causing any symptoms for a long time, which arguably represents the major challenge in early detection of meningiomas (2). Intriguingly, recurrence frequently occurs in tumors with benign histology, and recent studies revealed that coexistence of del(1p36) and monosomy 14 is associated with early recurrence of meningiomas (3). Mutations or deletions on the NF2 gene, which is located on 22q12.2 locus and encodes Merlin, have been originally described in meningiomas as an oncogenic driver gene (4). However, recent studies showed that other genetic alterations in TRAF7, PIK3CA, KLF4, POLR2A AKT1, SMO, SUFU, and SMARCB1 genes are involved in meningioma pathogenesis (5-8). Grade II and III meningiomas are also associated with few specific recurrent somatic mutations, such as SMARCE1 mutations in clear cell meningioma and BAP1 mutation in a subset of rhabdoid meningiomas (9). Treatment protocol for meningiomas is closely associated with tumor location, grade and includes surgery followed by fractionated external beam radiation therapy (EBRT) (10).

To date, no consensus has been established on specific biomarkers toward early diagnosis or prognosis for meningiomas. Most CNS tumors are currently diagnosed primarily radiology-based modalities like CT or MRI scans followed by validation with genetic or IHC-based diagnostic markers. The major challenge in the radiology-based technology is that the tumors can be detected only when they reach to a certain size, which creates worse prognostic risk as tumor is transformed from benign to malignant forms.

While CT and MRI are usually sufficient for diagnosis of meningiomas, other tumors and diseases may radiologically mimic meningioma and complicates the diagnosis (11). In addition, imaging modalities are only able to detect tumors when they reach a certain size. Given the slow growth rate of meningiomas, these tumors may remain undiagnosed for extended periods of time. Grade I meningiomas have a mean tumor age of >20 years, highlighting requirement of longer time periods to diagnose tumor. Furthermore, the average time between initial cell transformation and detection of tumor mass has been reported as 26.3 years in fibrous meningiomas, and 17.8 years in meningothelial meningiomas (12). Slow growth rate of meningiomas also complicates early prediction of the meningioma progression, and recurrence that occurs in ~30% of Grade I meningiomas, 50% of Grade II and 80% of Grade III meningiomas (13, 14).

Currently, there is no serum-based diagnostic and/or prognostic marker available to monitor transition stages of meningiomas from benign state to malignant form. Identification of such markers would not only improve early detection of meningioma, but also improve survival rate of meningioma patients.

Proteomics analysis has been used to investigate disease pathophysiology and identify potential surrogate disease markers for brain tumors (15-18). However, only a small number of reports focused on protein profiling of meningioma tumor specimens (19, 20) and serum samples (21). The majority of proteomics studies employed meningioma tumor tissues (22-25), while others used biological fluids, such as cerebrospinal fluid and serum (21).

In this study, for the search of biomarkers for meningiomas, a high-throughput, multiplex immunoassay cancer panel based on the proximity extension assay (PEA) was used to screen a set of 92 cancer-related protein markers. The serum protein expression profiles of Grade I (benign, n=23), Grade II (atypical, n=4), and Grade III (anaplastic, n=3) meningioma patients were analyzed in relation to the healthy control subjects (n=12). Furthermore, the validation studies using an independent set of meningioma tumor tissues (Grade I, n=20; Grade II, n=10; and Grade III, n=6) identifies a protein biomarker signature in meningioma patient sera.

Materials and Methods
Study Population

The screening cohort consisted of Grade I (n=23), Grade II (n=4), and Grade III (n=3) meningioma patients. The independent validation cohort consisted of Grade I (n=20), Grade II (n=10), Grade III (n=6) meningioma patient tissue samples that were collected after the surgery and stored at −80° C. Patients were operated at the Vienna General Hospital (Vienna, Austria). This study was carried out in accordance with the Good Scientific Practice recommendations of the ethics committee of Medical University of Vienna. All subjects gave written informed consent in accordance with the Declaration of Helsinki. The protocol was approved by the local ethics committee of the Medical University of Vienna.

Serum Collection

Preoperative blood samples were collected before any therapeutic intervention (surgery, chemotherapy, radiotherapy). Blood samples were let to stand at 4° C. for 60 min, and then centrifuged at 1,100×g for 10 min. Serum samples were aliquoted and stored at −80° C.

Protein Detection with Proximity Extension Assay (PEA)

Serum samples from Grade I (n=23), Grade II (n=4), and Grade III (n=3) meningioma patients were delivered to AIT Molecular Diagnostics. Age- and gender-matched control serum samples (n=12) were provided by AIT Molecular Diagnostics. OLINK ProSeek Oncology-I Panel was used to detect expression of 92 cancer-related proteins (olink.com/products/oncology) (Table S1). Briefly, 1 μL serum samples were incubated with 92 antibody pairs of oligonucleotide labeled antibodies. Binding of the antibody pair to the antigen brings the oligonucleotides to close proximity, and a new PCR target sequence is formed by a proximity dependent DNA polymerization event. The resulting sequence is subsequently detected and quantified by high throughput realtime PCR (BioMark™HD System, Fluidigm Corporation). The fluorescent signals generated in real-time PCR directly correlates with protein abundance. Raw Cq values were normalized by subtracting the Cq values for the extension control and compared to that of the corresponding background reaction. The resulting ddCq values were used for further analysis and represented as Normalized Protein Expression (NPE) in Log 2 scale.

TABLE S1

Protein markers included in the ProSeek Oncology-I Panel

| | |
|---|---|
| 01_IL-8 | 51_CXCL10 |
| 02_VEGF-A | 52_Ep-CAM |
| 03_Adrenomedullin | 53_ErbB2/Her2 |

TABLE S1-continued

Protein markers included in the ProSeek Oncology-I Panel

| | |
|---|---|
| 05_CD40 ligand | 54_ErbB3/Her3 |
| 06_GIN-15 | 55 ErbB4/Her4 |
| 07_PIGF | 56_J-IGF |
| 08_E-selectin | 57_PSA |
| 09_EGF | 58_MYD88 |
| 10 Osteoprotegerin | 59 MIA |
| 11_IFN-gamma | 60_CCL24 |
| 12_IL-1ra | 61_Midkine |
| 13 IL-6 | 62 U-PAR |
| 14_Cystatin B | 63_CXCL5 |
| 15_MCP-1 | 64_Cathepsin Dec |
| 16_Kallikrein-6 | 65_Betacellulin |
| 17_Galetin-3 | 66 Epiregulin |
| 18_EPO | 67_Flt3L |
| 20_LAP TGF-beta-1 | 68_VEGFR-2 |
| 21_Kallikrein-11 | 69_CCL21 |
| 22_TIE2 | 70_Caspase-3 |
| 23_Tissue Factor | 71_CD69 |
| 24_TNF-RI | 72_TNTRSF4 |
| 25_PDGF subunit B | 73_TR-AP |
| 26 GM-CSF | 74 CD30-L |
| 27_CSF-1 | 75_REG-4 |
| 28_CXCL11 | 76_TGF-alpha |
| 29 IL-12 | 77 Amphiregulin |
| 30_IL-2 | 78_HB-EGF |
| 31_IL-7 | 79_MIC-A |
| 32_Stem cell factor | 80_IL-4 |
| 33 CXCL9 | 81 VEGF-D |
| 34_IL6RA | 82_HE4 |
| 35_TNF-R2 | 83_CXCL13 |
| 36_MMP-3 | 84_EGFR |
| 37_IL2RA | 85_HGF receptor |
| 38-TNFSF14 | 86_Thrombopoietin |
| 39_Prolactin | 87_FABP4 |
| 40 MPO | 88 CEA |
| 41_Growth Hormone | 89_TNF |
| 42_FasL | 90_CA242 |
| 43_BAFF | 91_CA-125 |
| 44 FAS | 92 Prostasin |
| 45_CCL9 | 93_Follistatin |
| 48_Estrogen receptor | 94_PECAM-1 |
| 49 EMMPRIN | 95 IL17RB |
| 50_CAIX | 96_FR-alpha |

TABLE S3

Primers used in RT-qPCR experiments

| Target gene | Strand | Sequence |
|---|---|---|
| GAPDH | Forward | ACATCGCTCAGACACCATG (SEQ ID NO: 1) |
| | Reverse | TGTAGTTGAGGTCAATGAAGGG (SEQ ID NO: 2) |
| HB-ECF | Forward | GATCTGGACCTTTTGAGAGTCA (SEQ ID NO: 3) |
| | Reverse | TGCAGAAGTCCTTGTATTTCCG (SEQ ID NO: 4) |
| AR | Forward | GCTGTCGCTCTTGATACTCG (SEQ ID NO: 5) |
| | Reverse | CTTCCCAGAGTAGGTGTCATTG (SEQ ID NO: 6) |
| CD69 | Forward | ACATGGTGCTACTCTTGCTG (SEQ ID NO: 7) |
| | Reverse | CTTTGCCATTTGACCACTTCC (SEQ ID NO: 8) |
| VEGFD | Forward | AATTAGTGCCTGTTAAAGTTGCC (SEQ ID NO: 9) |
| | Reverse | AGGACAGAGTTTCTTGGAATGG (SEQ ID NO: 10) |
| E-Selectin | Forward | TTGCAAGTGTGACCCTGG (SEQ ID NO: 11) |
| | Reverse | TGTAGCTGAAGTTTCCCAGTG (SEQ ID NO: 12) |
| Prolactin | Forward | AACCAAACGGCTTCTAGAGG (SEQ ID NO: 13) |
| | Reverse | ATAAGCAGAAAGGCGAGACTC (SEQ ID NO: 14) |
| BAFF | Forward | ACGCCATGGGACATCTAATTC (SEQ ID NO: 15) |
| | Reverse | TTCCAGTTTTGCAATGCCAG (SEQ ID NO: 16) |

Functional Analysis

Differentially expressed proteins (FDR=0.01) identified in Reproducibility-optimized test statistic (ROTS) were analyzed with the PANTHER database version 14.0 (http://www.pantherdb.org/) (26). The list of proteins was uploaded and mapped against the reference dataset (*Homo sapiens*).

Real Time-qPCR

High-Capacity cDNA Reverse Transcription Kit (Applied Biosystems) was used to reverse transcribe 1,000 ng of total RNA. Quantitative real-time PCR reactions were performed using the Universal PCR Master Mix (Thermo Scientific) on a 7300 Real-Time PCR system (Applied Biosystems). ΔCt values were calculated according to the following formula (27): $\Delta Ct = Ct_{Target} - CT_{Reference}$. This equation considers Ct values to be proportional to the negative logarithm of gene expression. Thus, ΔCt values are positively related to the expression of gene of interest. Glyceraldehyde 3-phosphate dehydrogenase (GAPDH) was used as a reference gene to normalize gene expression. Primer sequences are shown in Table S3.

Western Blotting

Western blotting was performed as previously described (28). The following primary antibodies were used: Caspase-3 (1:2,000, BD Biosciences) and beta-actin (1:5,000, Sigma-Aldrich). Densitometric analysis was performed on scanned blot images. Images were transformed to grayscale on ImageJ software (v. 1.50i, National Institutes of Health, USA). For each blot, a lane normalization factor was calculated by dividing the signal of each loading control band with that of the highest signal of loading control on the blot. The calculated lane normalization factor was then used to normalize caspase 3 band signals.

Statistical Analysis

Reproducibility-optimized test statistic (ROTS) algorithm (26) was used to identify differentially expressed proteins. Comparisons were done between Grade I preoperative samples and control samples. The default parameters (B=1,000, K=19) were used for all comparisons. Proteins with a false discovery rate (FDR) below 0.01 were considered as significant. RStudio version 1.1.414 and Prism version 8.0.1 (GraphPad Inc.) were used for statistical analysis. Multiple tests (Anderson-Darling, D'Agostino and Pearson, Shapiro-Wilk, and Kolmogorov-Smirnov tests) were used to test for log-normal distribution. For proteins that followed normal distribution, paired t-test was used to compare protein expression between the samples. For proteins that did not follow normal distribution, Wilcoxon matched pairs signed rank test was used. Brown-Forsythe ANOVA test with Dunnett's multiple comparison was used to compare mRNA expression levels among meningioma grades. P<0.05 were considered statistically significant.

Results

Serum Protein Profiling with a High-Throughput, Multiplex Immunoassay Cancer Panel Using the Proximity Extension Assay To identify protein biomarkers associated with meningioma, a high-throughput, multiplex immunoassay cancer panel consisting of 92 putative cancer-related human proteins that are involved in key biological processes, such as angiogenesis, cell-to-cell signaling, cell-cycle control, and inflammation which play central roles in cancer metabolism was used. The putative protein biomarkers that are selected based on the analyses of commonly used bioinformatic databases (e.g., Uniprot, Human Protein Atlas, Gene Ontology (GO), and DisGeNET) are then classified according to their functional protein groups, roles in biological processes, associations with diseases, and expression patterns in tissues (Olink Proteomics) (Table S1). The multiplex nature of this immunoassay-based cancer panel enables simultaneous analysis of large sample numbers, and its coupling with the PEA technology provides uncompromised data quality. Thus, taking advantage of this technology, 30 serum samples obtained from meningioma patients prior to the surgery, and 12 control serum samples from the age- and gender-matched healthy subjects were analyzed.

Figures 1, 1B:
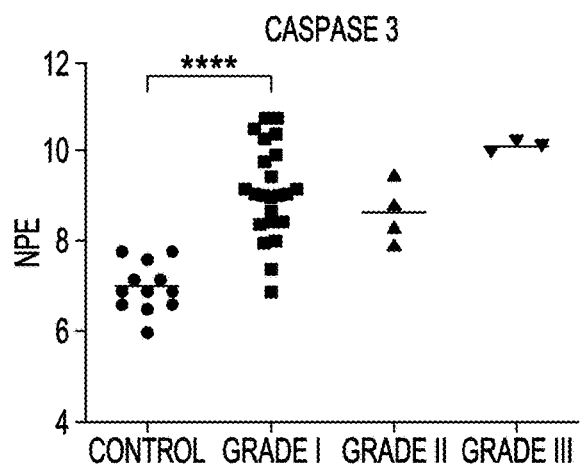
FIGS. 2A-1-2C Validation studies of cancer-panel protein screening candidates. For validation studies, by using an independent meningioma tissue specimen set, n=36 (Grade I (n=20), Grade II (n=10), and Grade III (n=6)), the expressions of the indicated genes were analyzed by RT-qPCR, Normal white matter (NWM) tissue samples were used as control (AREG, NWM vs. Grade I, **p<0.0001, Brown-Forsythe ANOVA test with Dunnett's multiple comparison; VEGF-D, NWM vs. Grade I, p<0.01, Brown-Forsythe ANOVA test with Dunnett's multiple comparison) (A). Western blot images showing caspase-3 protein expression in tumor lysates obtained from Grade I (n=18), Grade II (n=10), and Grade III (n=7) meningiomas (B). Densitometric analysis of Western blot bands (NWM vs. Grade I, ***p<0.001, Brown-Forsythe ANOVA test with Dunnett's multiple comparison; NWM vs. Grade II, and NWM vs. Grade III, *p<0.05, Brown-Forsythe ANOVA test with Dunnett's multiple comparison) (C).
Figures 1, 1B, 2:
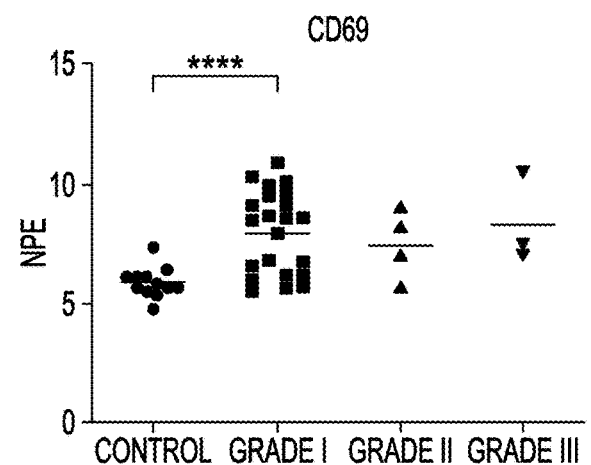
Figures 1, 1B, 2, 3:
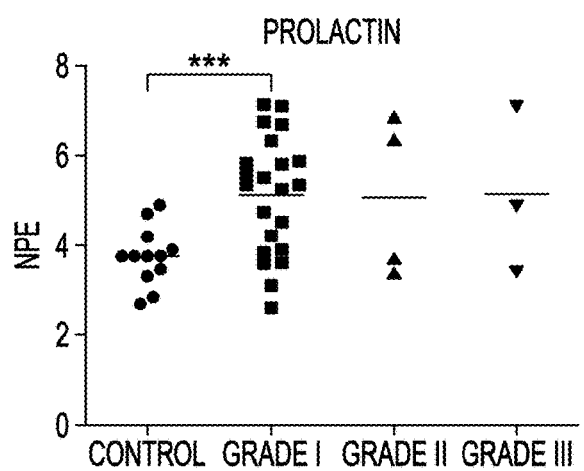
Figures 1, 1B, 2, 3, 4:
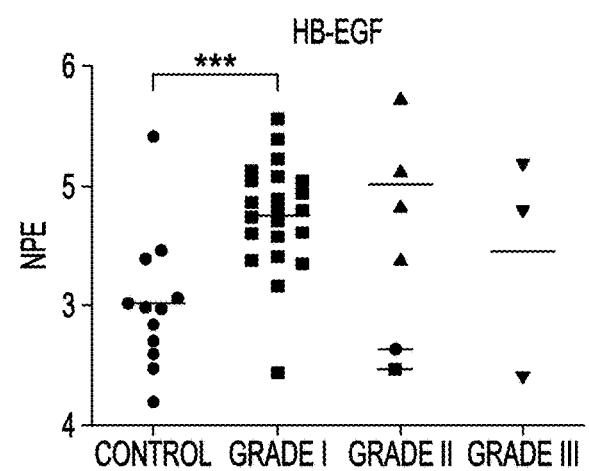
Figures 1, 1B, 2, 3, 4, 5:
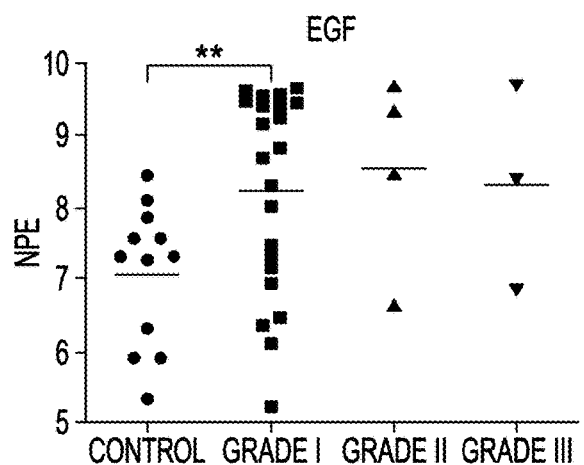
Figures 1, 1B, 2, 3, 4, 5, 6:
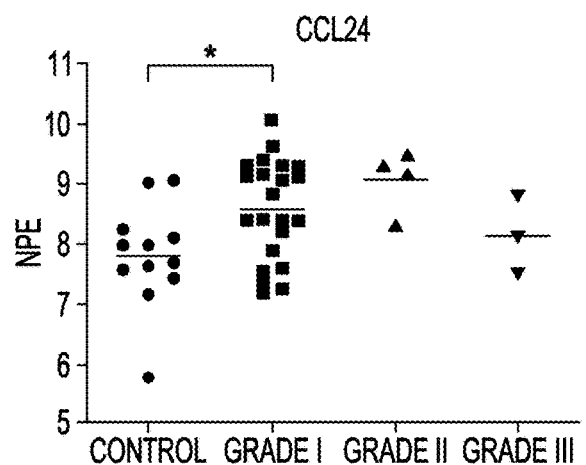
Figures 1, 1B, 2, 3, 4, 5, 6, 7:
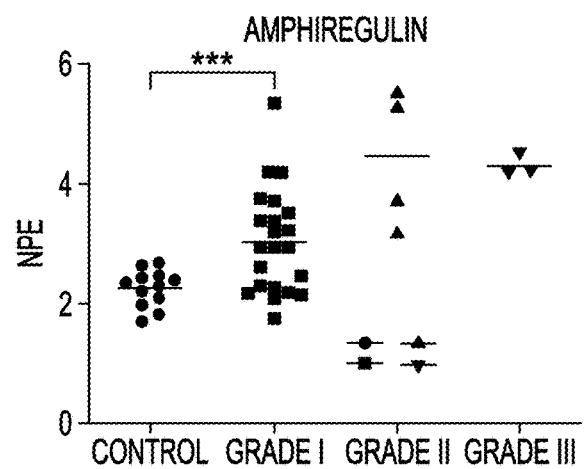
Figures 1, 1C:
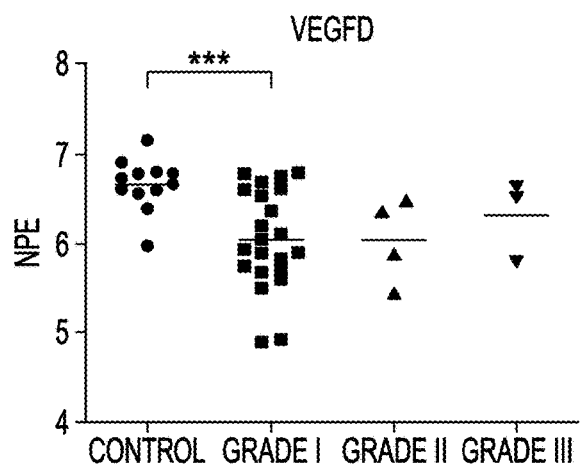
Figures 1, 1C, 2:
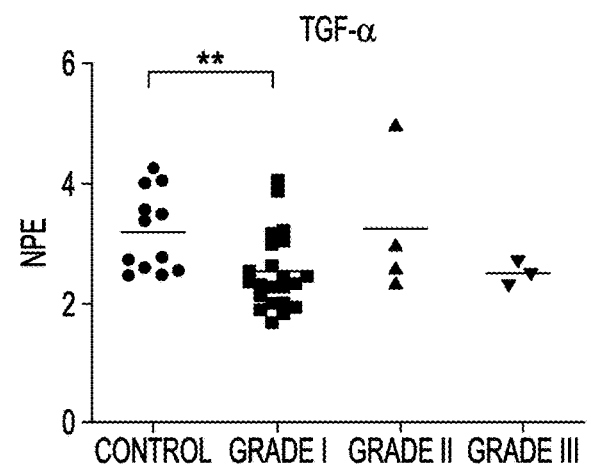
Figures 1, 1C, 2, 3:
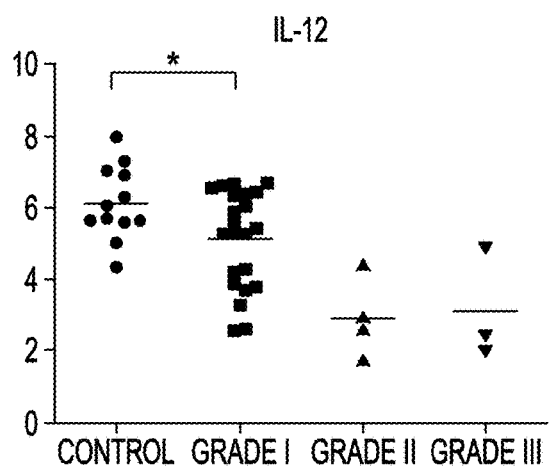
Figures 1, 1C, 2, 3, 4:
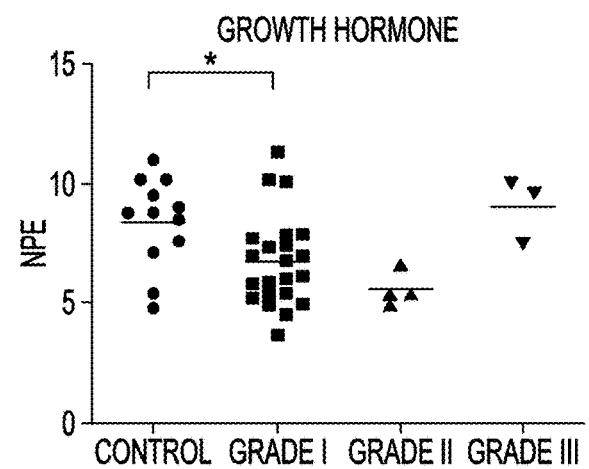
Figures 1, 1C, 2, 3, 4, 5:
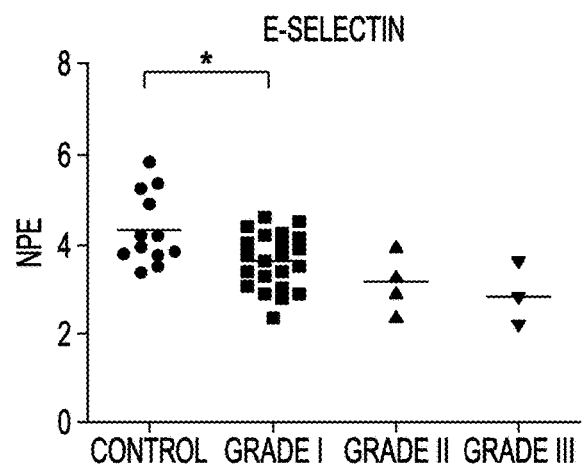
Figures 1, 1C, 2, 3, 4, 5, 6:
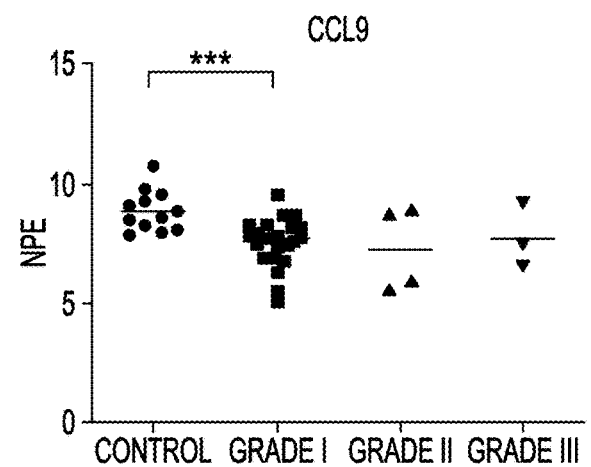
Figures 1, 1C, 2, 3, 4, 5, 6, 7:
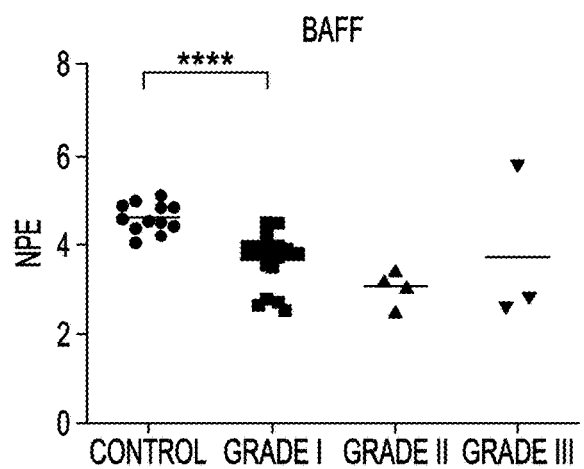

The results showed that 14 proteins were differentially expressed in the Grade I meningioma patients compared to healthy control subjects (FIG. 1). Of those, seven proteins, caspase-3, CD69, prolactin, epidermal growth factor (EGF), chemokine (C-C) ligand 24 (CCL24), amphiregulin (AREG), and heparin-binding EGF (HB-EGF) were highly expressed in the Grade I meningioma samples (FIG. 1B), while, the other seven proteins, vascular endothelial growth factor D (VEGFD), transforming growth factor alpha (TGF-α), E-selectin, B-cell activating factor (BAFF), interleukin-12 (IL-12), chemokine (C-C motif) ligand 9 (CCL9), and Growth Hormone were reduced in the meningioma serum samples, compared to healthy control subjects (FIG. 1C and Table 1). The PANTHER pathway analyses revealed that differentially expressed proteins are linked to the EGF receptor signaling (EGF, amphiregulin, HB-EGF, TGF-a), apoptosis (caspase-3), immunomodulation (prolactin, CD69, CCL24, IL-12, CCL9, BAFF), and angiogenesis (VEGF-D). Of note, the expression levels of 16 analytes were below the limit of detection in more than 20% of all samples. These markers were excluded from the downstream analyses (Table S2).

TABLE 1

Differentially expresso: proteins between Grade 1 meningioma patients and control subjects

| Protein | log2FC (Meningioma/ Control) | Linear FC (Meningioma/ Control) | P-value | FDR |
| --- | --- | --- | --- | --- |
| Caspase-3 | 2.13 | 4.38 | 0 | 0.00 |
| CD69 | 2.09 | 4.27 | 3.29E-05 | 0.00 |
| Prolactin | 1.37 | 2.58 | 4.47E-04 | 0.00 |
| EGF | 1.18 | 2.26 | 2.89E-03 | 0.00 |

TABLE 1-continued

Differentially expresso: proteins between Grade 1 meningioma patients and control subjects

| Protein | log2FC (Meningioma/ Control) | Linear FC (Meningioma/ Control) | P-value | FDR |
| --- | --- | --- | --- | --- |
| CCL24 | 0.79 | 1.72 | 8.68E-03 | 0.00 |
| Amphiregulin | 0.78 | 1.72 | 5.66E-03 | 0.00 |
| HB-EGF | 0.76 | 1.69 | 2.16E-03 | 0.00 |
| VEGFD | -0.61 | 0.66 | 8.64E-03 | 0.00 |
| TGF-α | -0.67 | 0.63 | 9.88E-03 | 0.00 |
| E-selectin | -0.69 | 0.62 | 9.55E-03 | 0.00 |
| BAFF | -0.93 | 0.53 | 4.54E-04 | 0.00 |
| IL-12 | -1.00 | 0.50 | 8.41E-03 | 0.00 |
| CCL9 | -1.33 | 0.40 | 2.89E-04 | 0.00 |
| Growth Hormone | -1.66 | 0.32 | 1.82E-03 | 0.00 |

PC, Fold Change; FDR, False Discovery Rate

TABLE S2

Protein markers excluded from analyses

| Protein | Number of samples at LOD | Percentage of samples at LOD |
| --- | --- | --- |
| 11_IFN-gamma | 43 | 60 |
| 18_EPO | 23 | 32 |
| 26_GM-CSF | 72 | 100 |
| 30_1L-2 | 72 | 100 |
| 36_MMP-3 | 26 | 36 |
| 48_Estrogen receptor | 72 | 100 |
| 57_PSA | 40 | 56 |
| 58_MYD88 | 18 | 25 |
| 65_Betacellulin | 71 | 99 |
| 66_Epiregulin | 26 | 36 |
| 80_IL-4 | 41 | 57 |
| 88_CEA | 52 | 72 |
| 89_TNF | 57 | 79 |
| 90_CA242 | 70 | 97 |
| 91_CA-125 | 30 | 42 |
|  | Number of samples with negative expression value | Percentage of samples with negative expression value |
| 79_MIC-A | 64 | 88 |

It was further questioned whether the differentially expressed proteins detected in the blood circulation of the meningioma patients were correlated with the tumor grade. Although the patterns of the protein profiles of the Grade II and Grade III patients were comparable to that of the Grade I patients, due to small sample size statistical analysis of the differences between these groups was not possible (Grade II (n=4) and Grade III (n=3) patients).

Validation Cohort Using an Independent
Set of Meningioma Tumor Tissues

Figures 1, 2A:
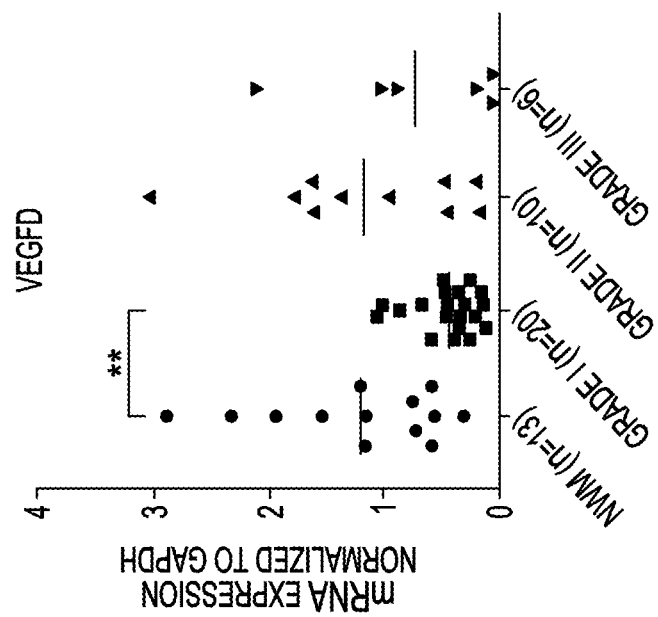
Figures 2, 2A:
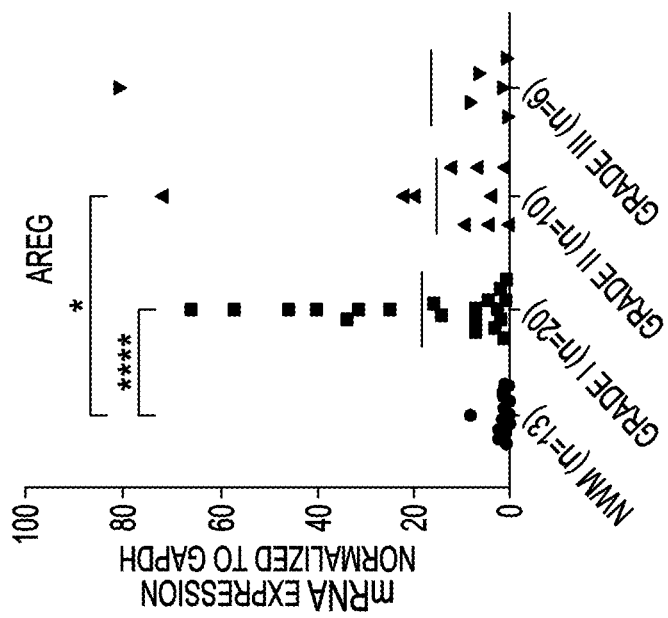
Figure 2C:
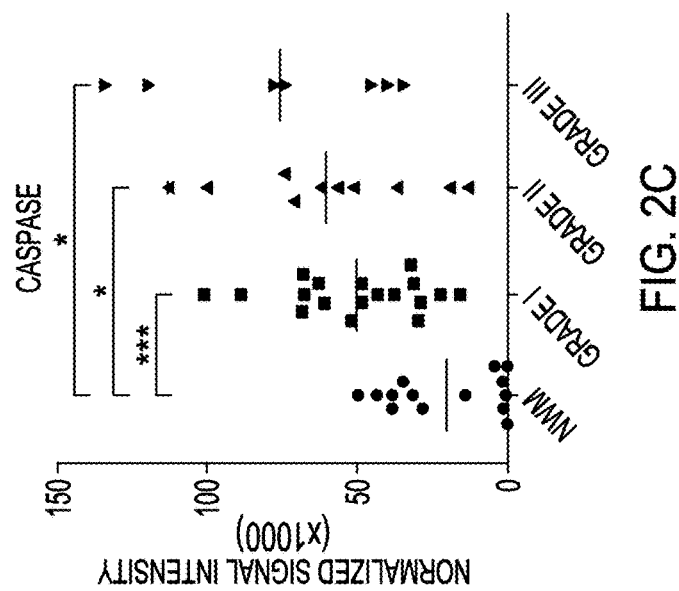
Figure 2B:
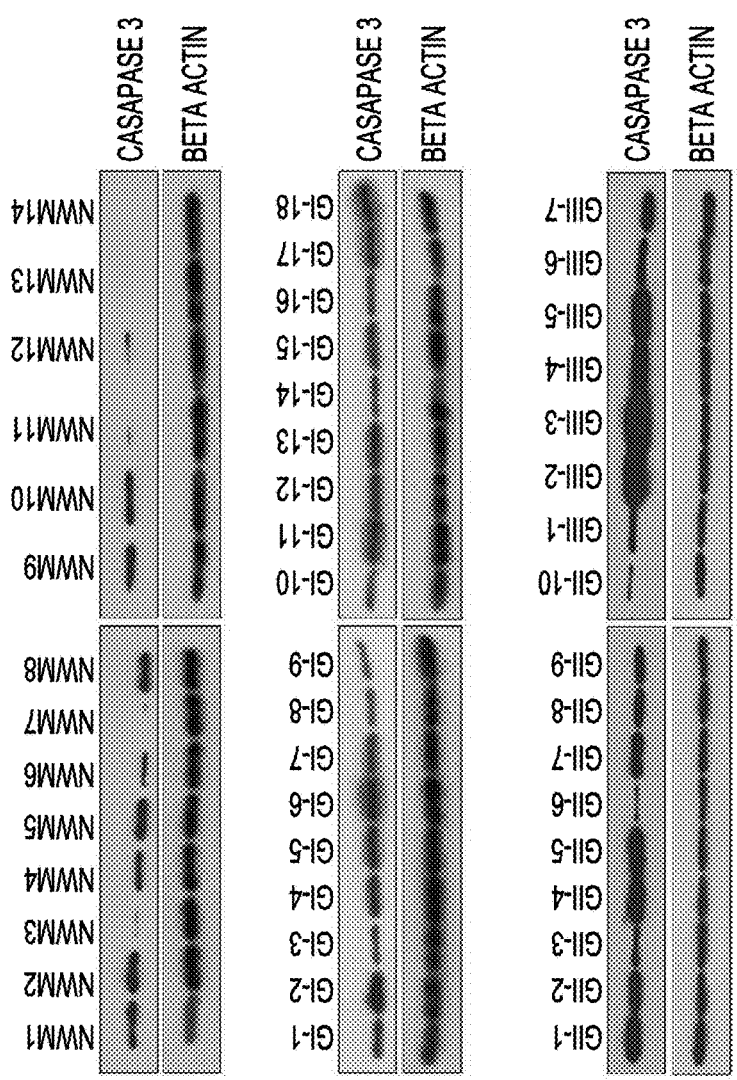
Figure 3C:
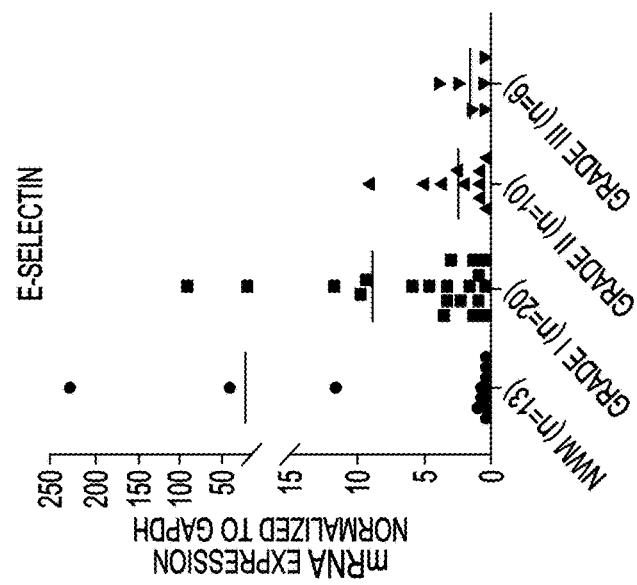
FIGS. 3A-3E RT-qPCR was used to analyze the mRNA expression of differentially expressed proteins in an independent validation cohort. In contrast with the screening results, prolactin and HB-EGF mRNA expression was lower in Grade I meningioma tumor tissues, whereas BAFF mRNA expression was higher in all grades. E-Selectin and CD69 mRNA expression matched the screening results, but the differences in mRNA expression levels were not statistically significant (Brown-Forsythe ANOVA test with Dunnett's multiple comparison, p>0.05).
Figure 3B:
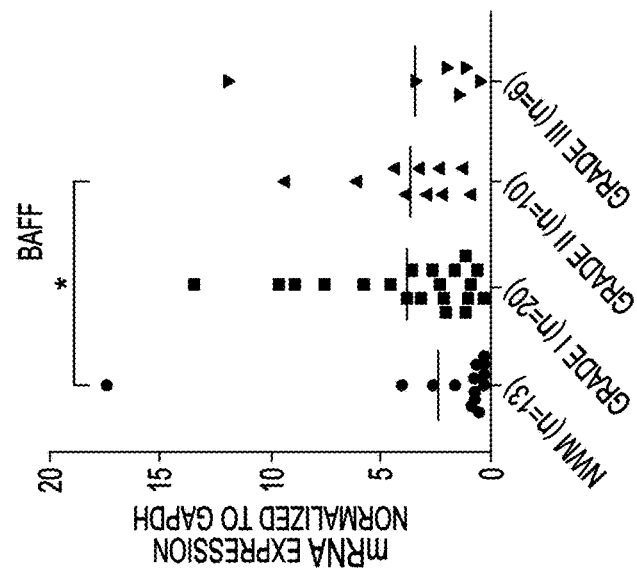
Figure 3A:
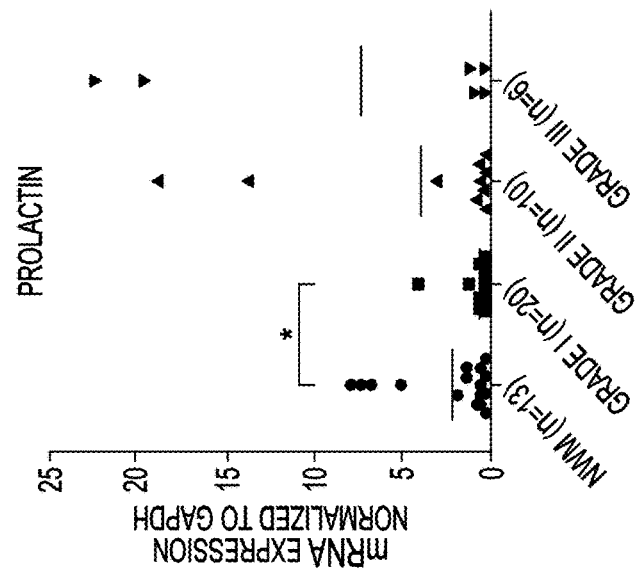
Figure 3E:
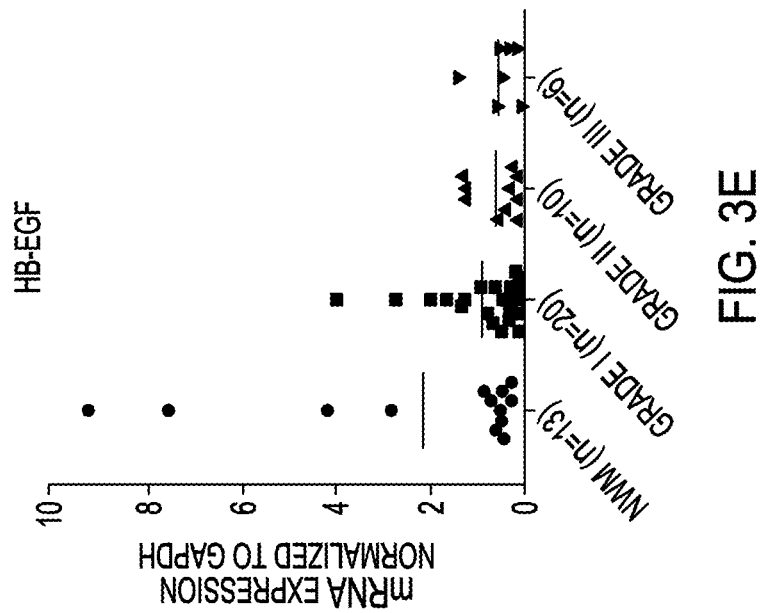
Figure 3D:
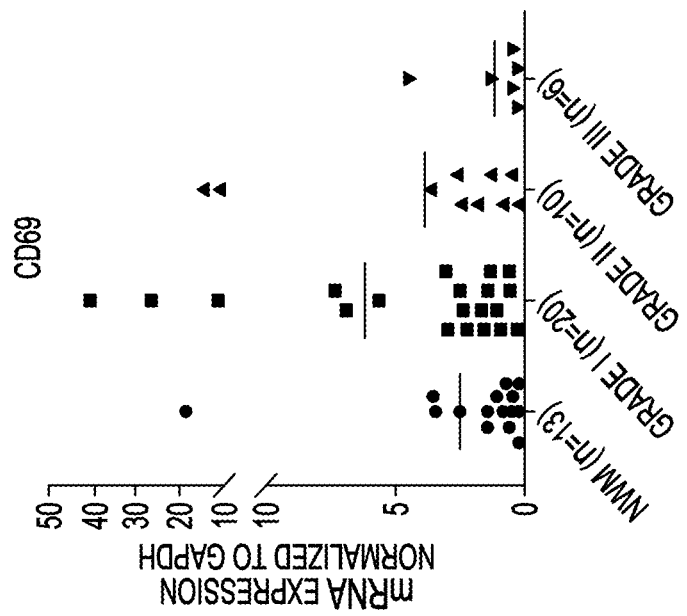

For validation studies, an independent set of 49 meningioma tissue samples were enrolled, including Grade I, n=20; Grade II, n=10; grade III, n=6, as well as Normal White Matter (NWM), n=13 as control tissue samples. As shown in FIG. 2A, a significant increase in the gene expression levels of amphiregulin was found in the Grade I meningiomas, while the VEGFD mRNA levels were relatively decreased, compared to the control NWM tissue samples. In addition, protein expression levels of Caspase 3 enzyme were analyzed in the tissue samples, and it was found that the protein levels of Caspase 3 are significantly higher in all grades of meningioma tissue samples compared to the control group (FIGS. 2B, C). A significant difference was not observed in the gene expression profiles of CD69, BAFF, HB-EGF, E-Selectin (FIG. 3) suggesting that these proteins may not exclusively originate from meningioma tumor cells, but rather may be secreted from other cell types, such as immune system cells that circulate in the bloodstream.

Discussion

Identification of non-invasive protein biomarkers has been a great interest for cancer diagnosis. Herein, cancer biomarkers are provided that can be used for diagnostic and prognostic purposes in meningioma patients. For this discovery study, we employed a commercial cancer panel based on a high-throughput, multiplex immunoassay that is equipped with the PEA technology was used, and serum protein profiles of the meningioma patients (n=30) in comparison to the control subjects (n=12) was detected. By taking advantage of the technology of PEA that requires low sample input to carry out multiplexed assays with good sensitivity and specificity (29, 30), 14 differentially expressed proteins in the sera of the Grade I meningioma patients relative to the healthy control subjects was identified (FIGS. 1A-C). In addition, the proteins differentially expressed in the Grade I meningioma patient sera were also detected in a small set of Grade II (n=4) and Grade III (n=3) patient sera (FIGS. 1A, B). However, due to the small sample size of higher-grade meningioma patient samples, we were unable to determine how significantly protein expressions differed between the tumor grades. In order to validate the potential biomarkers, an independent cohort containing 36 meningioma tumor samples was used, and it was found that amphiregulin and Caspase 3 are significantly increased in meningioma tumor tissues, while VEGF-D is relatively lower in comparison to the control NWM tissue samples (FIG. 2). The other candidate proteins, Prolactin, HB-EGF, E-Selectin, CD69, and BAFF that were emerged from the cancer-panel protein screening were not detected in the independent set of meningioma tissue specimens (FIG. 3).

In the study, caspase-3 emerged as a differentially expressed protein showing increased expression levels in the dataset of the meningioma patient sera (n=30). Caspase-3 is a central effector of apoptosis (31). However, sublethal activation of caspase-3 has been shown to promote genetic instability and carcinogenesis (32). In addition, caspase-3 was proposed to play a role in the repopulation of tumors in response to radiotherapy, and its activity is correlated with increased rate of recurrence and death in cancer patients (33). The findings showing increased serum levels of caspase-3 are supported by an earlier study reporting an increased caspase-3 immunoreactivity in meningioma tissues, in which Grade II and Grade III meningioma tissues exhibited higher scores of immunopositivity relative to the benign Grade I meningioma tissues (34). In addition, the same study identified caspase-3 as an independent predictor of early recurrence (34). Elevated serum caspase-3 levels in meningioma patients, along with its reported increased tissue levels indicate a clinical value for caspase-3 in meningioma as a predictive marker of benign-to-malignant transformation. In line with the instant study, a recent study has also shown that increased caspase-3 expression in primary atypical and malignant meningiomas is correlated with the higher grade of meningioma (35).

CD69, an early activation marker of lymphocytes and natural killer cells (36) is another hit detected in this screening study. CD69 is an important regulator of immune responses that take part in cytokine release, homing and migration of lymphocytes (37, 38). However, the state of tissue environment and cytokine spectrum could differentially regulate its role in immune responses (39). In murine models, CD69 deficiency is associated with enhanced antitumor immunity and longer survival (40). Recently, CD69 has been indicated in the induction of T cell exhaustion in a breast cancer tumor model in mice, where anti-CD69 antibody treatment was proven to enhance anti-tumor activity, pointing CD69 as a novel target for cancer immunotherapy (41). On the contrary, high levels of tumor infiltrating $CD4^+CD69^+$ T cells are associated with good prognosis in head and neck squamous cell carcinoma (42). In meningioma, an increased infiltration of $CD69^+$ lymphocytes, along with tissue macrophages and natural killer cells has been reported, which is specifically associated with the cases carrying a distinct cytogenetic profile of isolated monosomy 22/del(22q) that shows a better prognosis (43). Thus, increased infiltration of meningiomas by activated lymphocytes including $CD69^+$ subsets may be associated with immune surveillance, and elimination of tumor cells that restricts the tumor growth (43). Given that this study identified CD69 as a serum biomarker in meningiomas, it is plausible that this may be caused by the increased presence of tumor growth limiting $CD69^+$ lymphocytes in the circulation of Grade I meningioma patients.

The study identified two different ligands of EGFR, amphiregulin (AREG) and heparin-binding EGF (HB-EGF) that are elevated in the sera of Grade I meningioma patients. Among those, the validation studies showed that the expression of amphiregulin is significantly upregulated in the meningioma tumor tissues, compared to the control NWM specimens. Amphiregulin is a secreted EGFR ligand that regulates cellular growth and differentiation, immunity, inflammation, and tissue repair (44, 45), and it is overexpressed in a variety of cancers (44, 46, 47). Amphiregulin is originally described as an epithelial and mesenchymal cell-derived factor, however, recent studies show that it is expressed by multiple populations of activated immune cells including dendritic cells and CD4+ T cells (45). It is likely that elevated levels of amphiregulin in meningioma patient sera may reflect the response of immune system and/or the ongoing tissue repair owing to the tumor mass. Alternatively, amphiregulin and HB-EGF may act as activators of EGFR that is overexpressed in meningiomas, supporting tumor growth and malignancy (48).

Prolactin was found in elevated levels in the sera of the Grade I meningioma patient group in this study. However, an increase in prolactin levels was detected in meningioma tissues. Interestingly, some increase in prolactin receptor levels in meningiomas has been also reported earlier (49, 50).

CCL24 is a chemokine with well-studied roles in allergies (52). In the context of cancer, CCL24 expression has been shown to associate with poor prognosis in colorectal cancer and also contribute to hepatocellular carcinoma malignancy via the RhoB VEGFA-VEGFR2 angiogenesis pathway (53, 54). In this study, slightly higher serum levels of CCL24 in Grade I meningioma patients in comparison to the control subjects was detected.

IL-12 is a cytokine that is mainly produced by antigen presenting cells, and it has well-established anti-tumor activity (55, 56). IL-12 serum levels were found relatively reduced in meningioma and glioblastoma patients (57). Consistently, this study revealed that Grade I meningioma patients have reduced serum IL-12 levels compared to the control subjects.

VEGF plays a pivotal role in angiogenesis, and its expression in meningiomas was reported to associate with unfavorable prognosis and recurrence (58-60). Intriguingly, several studies addressing serum VEGF levels in meningioma depicted some contradictory results. Stockhammer et al. reported that serum VEGF-A concentration is higher in patients with central nervous system tumors, including meningioma, than in patients with no tumor diagnosis (61). Nowacka et al. reported higher serum VEGF-A levels in meningioma patients (62). In this study, it was detected that the serum levels of VEGF-D, a member of the VEGF family that plays a role in glioblastoma angiogenesis (63), is relatively lower in the Grade I meningioma patients compared to the control subjects. Furthermore, it was shown that the gene expression of VEGF-D is significantly lower in meningioma tumor tissues relative to the control NWM tissues. In line with the instant findings, another group reported lower serum levels of VEGF in meningioma patients where control subjects had higher levels of serum VEGF (64).

B-cell activating factor (BAFF), a member of the TNF superfamily is one of the critical factors controlling B-cell homeostasis, and its interaction with its ligand/receptor regulates the survival and proliferation of malignant cells (65, 66). High BAFF serum levels have been detected in autoimmune disorders, including rheumatoid arthritis and systemic lupus erythematosus, as well as in the malignancies, such as non-Hodgkin's lymphoma, B-CLL, and multiple myeloma (65). Interestingly, BAFF is expressed in astrocytes and astrocyte derived BAFF promotes B-cell survival in multiple sclerosis and primary CNS lymphoma (67). Herein the findings revealing low levels of circulating BAFF in Grade I meningioma indicate an autocrine control of the BAFF system that can counteract the malignant progression of meningiomas.

Similarly, it was observed that the patients with Grade I meningioma had lower levels of serum E-selectin, compared to the healthy control subjects. Given the roles of selectins in cancer progression and metastasis (68), low levels of E-selectin reflect the benign state of meningiomas.

Chemokines and their receptors play roles in determining the metastatic destination of cancers (69). Chemokine CCL9 (MIP-1g) is a ligand for the CCR1/CD191 receptor present on T cells, monocytes, macrophages, some myeloid-derived suppressor cells, and osteoclasts (70), and it is a potent chemo-attractant for immune cells (71). Moreover, CCL9/CCR1 signaling has been shown to recruit myeloid progenitors to tumor area, leading to progression of adenomas to carcinomas and also enhancing tumor invasion (70, 72-74). CCL9 has also been suggested as a fair candidate for anti-metastasis treatment of cancer (75). In this study, circulating CCL9 appeared to be lower in Grade I meningioma relative to the control group, in a similar way to the serum levels of VEGF, BAFF, E-selectin, and IL-12. Low serum levels of CCL9, VEGF, BAFF, E-selectin, and IL-12 can reflect the benign state of the disease that can be used for monitoring the tumor progression from benign to malignant form.

In sum, this study provides a list of proteins that can be utilized as diagnostic/prognostic circulating biomarkers of meningioma. The validation studies in an independent set of meningioma tissue specimens provide further evidence that caspase-3, amphiregulin and VEFG-D are markers to monitor the status of meningiomas through a non-invasive manner by using patient blood.

BIBLIOGRAPHY

1. Ostrom Q T, Gittleman H, Truitt G, Boscia A, Kruchko C, Barnholtz-Sloan J S. CBTRUS statistical report: primary brain and other central nervous system tumors diagnosed in the United States in 2011-2015. Neuro Oncol. (2018) 20:iv1-86. doi: 10.1093/neuonc/noy131
2. Gupta S, Mukherjee S, Syed P, Pandala N G, Choudhary S, Singh V A, et al. Evaluation of autoantibody signatures in meningioma patients using human proteome arrays. Oncotarget. (2017) 8:58443-56. doi: 10.18632/oncotarget.16997
3. Maillo A, Orfao A, Espinosa A B, Sayagues J M, Merino M, Sousa P, et al. Early recurrences in histologically benign/grade I meningiomas are associated with large tumors and coexistence of monosomy 14 and del(1p36) in the ancestral tumor cell clone. Neuro Oncol. (2007) 9:438-46. doi: 10.1215/15228517-2007-026
4. Trofatter J A, MacCollin M M, Rutter J L, Murrell J R., Duyao M P, Parry D M, et al. A novel moesin-, ezrin-, radixin-like gene is a candidate for the neurofibromatosis 2 tumor suppressor. Cell. (1993) 75:791-800. doi: 10.1016/0092-8674(93)90406-G
5. Abedalthagafi M, Bi W L, Aizer A A, Merrill P H, Brewster R, Agarwalla P K, et al. Oncogenic PI3K mutations are as common as AKT1 and SMO mutations in meningioma. Neuro Oncol. (2016) 18:649-55. doi: 10.1093/neuonc/nov316
6. Bacci C, Sestini R, Provenzano A, Paganini I, Mancini I, Porfirio B, et al. Schwannomatosis associated with multiple meningiomas due to a familial SMARCB1 mutation. Neurogenetics. (2010) 11:73-80. doi: 10.1007/s10048-009-0204-2
7. Brastianos P K, Horowitz P M, Santagata S, Jones R T, McKenna A, Getz G, et al. Genomic sequencing of meningiomas identifies oncogenic SMO and AKT1 mutations. Nat Genet. (2013) 45:285-9. doi: 10.1038/ng.2526
8. Clark V E, Erson-Omay E Z, Serin A, Yin J, Cotney J, Ozduman K, et al. Genomic analysis of non-NF2 meningiomas reveals mutations in TRAF7, KLF4, AKT1, and SMO. Science. (2013) 339:1077-80. doi: 10.1126/science.1233009
9. BiWL, WuWW, Santagata S, ReardonDA, Dunn I F. Checkpoint inhibition in meningiomas. Immunotherapy. (2016) 8:721-31. doi: 10.2217/imt-2016-0017
10. Rogers L, Barani I, Chamberlain M, Kaley T J, McDermott M, Raizer J, et al. Meningiomas: knowledge base, treatment outcomes, and uncertainties. A RANO Rev J Neurosurg. (2015) 122:4-23. doi: 10.3171/2014.7.JNS131644
11. Nowosielski M, Galldiks N, Iglseder S, Kickingereder P, von Deimling A, BendszusM, et al. Diagnostic challenges in meningioma. Neuro Oncol. (2017) 19:1588-98. doi: 10.1093/neuonc/nox101
12. Huttner H B, Bergmann O, Salehpour M, El Cheikh R, Nakamura M, Tortora A, et al. Meningioma growth dynamics assessed by radiocarbon retrospective birth dating. EBioMed. (2018) 27:176-81. doi: 10.1016/j.ebiom.2017.12.020
13. Adegbite A B, Khan M I, Paine K W, Tan L K. The recurrence of intracranial meningiomas after surgical treatment. J Neurosurg. (1983) 58:51-6. doi: 10.3171/jns.1983.58.1.0051
14. de Almeida A N, Pereira B J A, Pires Aguiar P H, PaivaWS, CabreraHN, da Silva C C, et al. Clinical outcome, tumor recurrence, and causes of death: a long-term follow-up of surgically treated meningiomas. World Neurosurg. (2017) 102:139-43. doi: 10.1016/j.wneu.2017.03.009
15. Gautam P, Nair S C, Gupta M K, Sharma R, Polisetty R V, Uppin M S, et al. Proteins with altered levels in plasma from glioblastoma patients as revealed by iTRAQ-based quantitative proteomic analysis. PLoS ONE. (2012) 7:e46153. doi: 10.1371/journal.pone.0046153

16. Gollapalli K, Ray S, Srivastava R, Renu D, Singh P, Dhali S, et al. Investigation of serum proteome alterations in human glioblastoma multiforme. Proteomics. (2012) 12:2378-90. doi: 10.1002/pmic.201200002

17. Ray S, Reddy P J, Jain R, Gollapalli K, Moiyadi A, Srivastava S. Proteomic technologies for the identification of disease biomarkers in serum: advances and challenges ahead. Proteomics. (2011) 11:2139-61. doi: 10.1002/pmic.201000460

18. Whittle I R, Short D M, Deighton R F, Kerr L E, Smith C, McCulloch J. Proteomic analysis of gliomas. Br J Neurosurg. (2007) 21:576-82. doi: 10.1080/02688690701721691

19. Herrmann A, Ooi J, Launay S, Searcy J L, Deighton R F, McCulloch J, et al. Proteomic data in meningiomas: post-proteomic analysis can reveal novel pathophysiological pathways. J Neurooncol. (2011) 104:401-10. doi: 10.1007/s11060-010-0526-9

20. Saydam O, Senol O, Schaaij-Visser T B, Pham T V, Piersma S R, Stemmer-Rachamimov A O, et al. Comparative protein profiling reveals minichromosome maintenance (MCM) proteins as novel potential tumor markers for meningiomas. J Proteome Res. (2010) 9:485-94. doi: 10.1021/pr900834h 21. Sharma S, Ray S, Moiyadi A, Sridhar E, Srivastava S. Quantitative proteomic analysis of meningiomas for the identification of surrogate protein markers. Sci Rep. (2014) 4:7140. doi: 10.1038/srep07140

22. Bouamrani A, Ramus C, Gay E, Pelletier L, Cubizolles M, Brugiere S, et al. Increased phosphorylation of vimentin in noninfiltrative meningiomas. PLoS ONE. (2010) 5:e9238. doi: 10.1371/journal.pone.0009238

23. Okamoto H, Li J, Vortmeyer A O, Jaffe H, Lee Y S, Glasker S, et al. Comparative proteomic profiles of meningioma subtypes. Cancer Res. (2006) 66:10199-204. doi: 10.1158/0008-5472.CAN-06-0955

24. Parada C A, Osbun J, Kaur S, Yakkioui Y, Shi M, Pan C, et al. Kinome and phosphoproteome of high-grade meningiomas reveal AKAP12 as a central regulator of aggressiveness and its possible role in progression. Sci Rep. (2018) 8:2098. doi: 10.1038/s41598-018-19308-y 25. Varlotto J, Flickinger J, Pavelic M T, Specht C S, Sheehan J M, Timek D T, et al. Distinguishing grade I meningioma from higher grade meningiomas without biopsy. Oncotarget. (2015) 6:38421-8. doi: 10.18632/oncotarget.5376

26. Suomi T, Seyednasrollah F, Jaakkola M K, Faux T, Elo L L. ROTS: An R package for reproducibility-optimized statistical testing PLoS Comput Biol. (2017) 13:e1005562. doi: 10.1371/journal.pcbi.10 05562

27. Jones M R, Dilai S, Lingampally A, Chao C M, Danopoulos S, Cararo G, et al. A comprehensive analysis of fibroblast growth factor receptor 2b signaling on epithelial tip progenitor cells during early mouse lung branching morphogenesis. Front Genet. (2018) 9:746. doi: 10.3389/fgene.2018.00746

28. Strobel T, Madlener S, Tuna S, Vose S, Lagerweij T, Wurdinger T, et al. Ape1 guides DNA repair pathway choice that is associated with drug tolerance in glioblastoma. Sci Rep. (2017) 7:9674. doi: 10.1038/s41598-017-10013-w 29. Assarsson E, Lundberg M, Holmquist G, Bjorkesten J, Thorsen S B, Ekman D, et al. Homogenous 96-plex PEA immunoassay exhibiting high sensitivity, specificity, and excellent scalability. PLoS ONE. (2014) 9:e95192. doi: 10.1371/journal.pone.0095192

30. Thorsen S B, Lundberg M, Villablanca A, Christensen S L, Belling K C, Nielsen B S, et al. Detection of serological biomarkers by proximity extension assay for detection of colorectal neoplasias in symptomatic individuals. J Transl Med. (2013) 11:253. doi: 10.1186/1479-5876-11-253

31. Taylor R C, Cullen S P, Martin S J. Apoptosis: controlled demolition at the cellular level. Nat Rev Mol Cell Biol. (2008) 9:231-41. doi: 10.1038/nrm2312

32. Liu X, He Y, Li F, Huang Q, Kato T A, Hall R P, et al. Caspase-3 promotes genetic instability and carcinogenesis. Mol Cell. (2015) 58:284-96. doi: 10.1016/j.molcel.2015.03.003

33. Huang Q, Li F, Liu X, Li W, Shi W, Liu F F, et al. Caspase 3-mediated stimulation of tumor cell repopulation during cancer radiotherapy. Nat Med. (2011) 17:860-6. doi: 10.1038/nm.2385

34. Konstantinidou A E, Givalos N, Gakiopoulou H, Korkolopoulou P, Kotsiakis X, Boviatsis E, et al. Caspase-3 immunohistochemical expression is a marker of apoptosis, increased grade and early recurrence in intracranial meningiomas. Apoptosis. (2007) 12:695-705. doi: 10.1007/s10495-006-0001-4

35. Vranic A. Caspase-3 and survivin expression in primary atypical and malignant meningiomas. ISRN Neurosci. (2013) 2013:626290. doi: 10.1155/2013/626290

36. Gonzalez-Amaro R, Cortes J R, Sanchez-Madrid F, Martin P. Is CD69 an effective brake to control inflammatory diseases? Trends Mol Med. (2013) 19:625-32. doi: 10.1016/j.molmed.2013.07.006

37. Radulovic K, Rossini V, Manta C, Holzmann K, Kestler H A, Niess J H. The early activation marker CD69 regulates the expression of chemokines and CD4 T cell accumulation in intestine. PLoS ONE. (2013) 8:e65413. doi: 10.1371/journal.pone.0065413

38. Shiow L R, Rosen D B, Brdickova N, Xu Y, An J, Lanier L L, et al. CD69 acts downstream of interferon-alpha/beta to inhibit S1P1 and lymphocyte egress from lymphoid organs. Nature. (2006) 440:540-4. doi: 10.1038/nature04606

39. Cibrian D, Sanchez-Madrid F. CD69: from activation marker to metabolic gatekeeper. Eur J Immunol. (2017) 47:946-53. doi: 10.1002/eji.201 646837

40. Esplugues E, Sancho D, Vega-Ramos J, Martinez C, Syrbe U, Hamann A, et al. Enhanced antitumor immunity in mice deficient in CD69. J Exp Med. (2003) 197:1093-106. doi: 10.1084/jem.20021337

41. Mita Y, Kimura M Y, Hayashizaki K, Koyama-Nasu R, Ito T, Motohashi S, et al. Crucial role of CD69 in anti-tumor immunity through regulating the exhaustion of tumor-infiltrating T cells. Int Immunol. (2018) 30:559-67. doi: 10.1093/intimm/dxy050

42. Badoual C, Hans S, Rodriguez J, Peyrard S, Klein C, Agueznay Net H, et al. Prognostic value of tumor-infiltrating CD4+ T-cell subpopulations in head and neck cancers. Clin Cancer Res. (2006) 12:465-72. doi: 10.1158/1078-0432.CCR-05-1886

43. Domingues P H, Teodosio C, Otero A, Sousa P, Ortiz J, Macias Mdel C, et al. Association between inflammatory infiltrates and isolated monosomy 22/del(22q) in meningiomas. PLoS ONE. (2013) 8:e74798. doi: 10.1371/journal.pone.0074798

44. Busser B, Sancey L, Brambilla E, Coll J L, Hurbin A. The multiple roles of amphiregulin in human cancer. Biochim Biophys Acta. (2011) 1816:119-31. doi: 10.1016/j.bbcan.2011.05.003

45. Zaiss D M W, Gause W C, Osborne L C, Artis D. Emerging functions of amphiregulin in orchestrating immunity, inflammation, and tissue repair. Immunity. (2015) 42:216-26. doi: 10.1016/j.immuni.2015.01.020
46. Berasain C, Avila M A. Amphiregulin. Semin Cell Dev Biol. (2014) 28:31-41. doi: 10.1016/j.semcdb.2014.01.005
47. Xu Q, Chiao P, Sun Y. Amphiregulin in cancer: new insights for translational medicine. Trends Cancer. (2016) 2:111-3. doi: 10.1016/j.trecan.2016.02.002
48. Arnli M B, Backer-Grondahl T, Ytterhus B, Granli U S, Lydersen S, Gulati S, et al. Expression and clinical value of EGFR in human meningiomas. PeerJ. (2017) 5:e3140. doi: 10.7717/peerj.3140
49. Ciccarelli E, Razzore P, Gaia D, Todaro C, Longo A, Forni M, et al. Hyperprolactinaemia and prolactin binding in benign intracranial tumours. J Neurosurg Sci. (2001) 45:70-4.
50. Muccioli G, Ghe C, Faccani G, Lanotte M, Forni M, Ciccarelli E. Prolactin receptors in human meningiomas: characterization and biological role. J Endocrinol. (1997) 153:365-71. doi: 10.1677/joe.0.1530365
51. Jimenez-Hakim E, el-Azouzi M, and Black P M. The effect of prolactin and bombesin on the growth of meningioma-derived cells in monolayer culture. J Neurooncol. (1993) 16:185-90. doi: 10.1007/BF01057032
52. Bisset L R, Schmid-Grendelmeier P. Chemokines and their receptors in the pathogenesis of allergic asthma: progress and perspective. Curr Opin Pulm Med. (2005) 11:35-42. doi: 10.1097/01.mcp.0000144502.50149.e0
53. Cheadle E J, Riyad K, Subar D, Rothwell D G, Ashton G, Batha H, et al. Eotaxin-2 and colorectal cancer: a potential target for immune therapy. Clin Cancer Res. (2007) 13:5719-28. doi: 10.1158/1078-0432.CCR-07-1145
54. Jin L, Liu W R, Tian M X, Jiang X F, Wang H, Zhou P Y, et al. CCL24 contributes to HCC malignancy via RhoB-VEGFA-VEGFR2 angiogenesis pathway and indicates poor prognosis. Oncotarget. (2017) 8:5135-48. doi: 10.18632/oncotarget.14095
55. Ngiow S F, Teng M W, Smyth M J. A balance of interleukin-12 and -23 in cancer. Trends Immunol. (2013) 34:548-55. doi: 10.1016/j.it.2013.07.004
56. Tugues S, Burkhard S H, Ohs I, Vrohlings M, Nussbaum K, Vom Berg J, et al. New insights into IL-12-mediated tumor suppression. Cell Death Differ. (2015) 22:237-46. doi: 10.1038/cdd.2014.134
57. Kumar R, Kamdar D, Madden L, Hills C, Crooks D, O'Brien D, et al. Th1/Th2 cytokine imbalance in meningioma, anaplastic astrocytoma and glioblastoma multiforme patients. Oncol Rep. (2006) 15:1513-6. doi: 10.3892/or.15.6.1513
58. Pfister C, Pfrommer H, Tatagiba M S, Roser F. Vascular endothelial growth factor signals through platelet-derived growth factor receptor beta in meningiomas in vitro. Br J Cancer. (2012) 107:1702-13. doi: 10.1038/bjc.2012.459
59. Pistolesi S, Boldrini L, Gisfredi S, De Ieso K, Camacci T, Caniglia M, et al. Angiogenesis in intracranial meningiomas: immunohistochemical and molecular study. Neuropathol Appl Neurobiol. (2004) 30:118-25. doi: 10.1046/j.0305-1846.2003.00516.x
60. Preusser M, Hassler M, Birner P, Rudas M, Acker T, Plate K H, et al. Microvascularization and expression of VEGF and its receptors in recurring meningiomas: pathobiological data in favor of anti-angiogenic therapy approaches. Clin Neuropathol. (2012) 31:352-60. doi: 10.5414/NP300488
61. Stockhammer G, Obwegeser A, Kostron H, Schumacher P, Muigg A, Felber S, et al. Vascular endothelial growth factor (VEGF) is elevated in brain tumor cysts and correlates with tumor progression. Acta Neuropathol. (2000) 100:101-5. doi: 10.1007/s004010051199
62. Nowacka A, Smuczynski W, Rosc D, Wozniak-Dabrowska K, Sniegocki M. SerumVEGF-A concentrations in patients with central nervous system (CNS) tumors. PLoS ONE. (2018) 13:e0192395. doi: 10.1371/journal.pone.0192395
63. Debinski W, Slagle-Webb B, Achen M G, Stacker S A, Tulchinsky E, Gillespie G Y, et al. VEGF-D is an X-linked/AP-1 regulated putative oncoangiogen in human glioblastoma multiforme. Mol Med. (2001) 7:598-608. doi: 10.1007/BF03401866
64. Park S H, Hwang J H, Hwang S K. Change in plasma vascular endothelial growth factor after gamma knife radiosurgery for meningioma: a preliminary study. J Korean Neurosurg Soc. (2015) 57:77-81.doi: 10.3340/jkns.2015.57.2.77
65. Ng L G, Mackay C R, Mackay F. The BAFF/APRIL system: life beyond B lymphocytes. Mol Immunol. (2005) 42:763-72. doi: 10.1016/j.molimm.2004.06.041
66. Sakai J, Akkoyunlu M. The role of BAFF system molecules in host response to pathogens. Clin Microbiol Rev. (2017) 30:991-1014. doi: 10.1128/CMR.00046-17
67. Krumbholz M, Theil D, Derfuss T, Rosenwald A, Schrader F, Monoranu C M, et al. BAFF is produced by astrocytes and up-regulated in multiple sclerosis lesions and primary central nervous system lymphoma. J Exp Med. (2005) 201:195-200. doi: 10.1084/jem.20041674
68. Laubli H, Borsig L. Selectins promote tumor metastasis. Semin Cancer Biol. (2010) 20:169-77. doi: 10.1016/j.semcancer.2010.04.005
69. Sheu B C, Chang W C, Cheng C Y, Lin H H, Chang D Y, Huang S C. Cytokine regulation networks in the cancer microenvironment. Front Biosci. (2008) 13:6255-68. doi: 10.2741/3152
70. Koizumi K, Hojo S, Akashi T, Yasumoto K, Saiki I. Chemokine receptors in cancer metastasis and cancer cell-derived chemokines in host immune response. Cancer Sci. (2007) 98:1652-8. doi: 10.1111/j.1349-7006.2007.00606.x
71. White G E, Iqbal A J, Greaves D R. C C chemokine receptors and chronic inflammation-therapeutic opportunities and pharmacological challenges. Pharmacol Rev. (2013) 65:47-89. doi: 10.1124/pr.111.0 05074
72. Hirai H, Fujishita T, Kurimoto K, Miyachi H, Kitano S, Inamoto S, et al. CCR1-mediated accumulation of myeloid cells in the liver microenvironment promoting mouse colon cancer metastasis. Clin Exp Metastasis. (2014) 31:977-89. doi: 10.1007/s10585-014-9684-z
73. Kitamura T, Fujishita T, Loetscher P, Revesz L, Hashida H, Kizaka-Kondoh S, et al. Inactivation of chemokine (C-C motif) receptor 1 (CCR1) suppresses colon cancer liver metastasis by blocking accumulation of immature myeloid cells in a mouse model. Proc Natl Acad Sci USA. (2010) 107:13063-8. doi: 10.1073/pnas.1002372107
74. Kitamura T, Kometani K, Hashida H, Matsunaga A, Miyoshi H, Hosogi H, et al. SMAD4-deficient intestinal tumors recruit CCR1+ myeloid cells that promote invasion. Nature genetics. (2007) 39:467-75. doi: 10.1038/ng1997
75. Yan H H, Jiang J, Pang Y, Achyut B R, Lizardo M, Liang X, et al. CCL9 induced by TGFb signaling in myeloid cells enhances tumor cell survival in the premetastatic organ. Cancer Res. (2015) 75:5283-98. doi: 10.1158/0008-5472.CAN-15-2282-T The invention is described with reference to various embodiments and techniques. However, it should be understood that many variations and modifications may be made while remaining within its scope. All referenced publications, patents and patent documents, as well as accession number for DNA, RNA and protein sequences, are intended to be incorporated by reference, as though individually incorporated by reference.

What is claimed is:

1. A method to detect and treat a meningioma in a subject comprising obtaining a blood serum sample from a subject,
    measuring a level of amphiregulin, CCL24, CD69, EGF, HB-EGF, caspase-3, VEGFD, TGF-α, BAFF, CCL9, and/or GH in said sample; and
    comparing the level of amphiregulin, CCL24, CD69, EGF, HB-EGF, caspase-3, VEGF-D, TGF-α, BAFF, CCL9, and/or GH to a level of amphiregulin, CCL24, CD69, EGF, HB-EGF, caspase-3, VEGF-D, TGF-a, E-Selectin, BAFF, CCL9, and/or GH in a control serum sample,
    wherein an increase in levels of amphiregulin, CCL24, CD69, EGF, HB-EGF, and/or caspase-3 and/or a decrease in levels of VEGF-D, TGF-α, BAFF, CCL9, and GH as compared to a control indicates a meningioma is present in said subject, and
    administering to the subject with a meningioma a treatment, wherein the treatment comprises surgery, radiation, immunotherapy, chemotherapy or a combination thereof.

2. The method of claim 1, wherein the level of caspase-3, amphiregulin and VEGF-D are detected.

3. The method of claim 1, wherein the measuring is achieved with an immunoassay selected from a group consisting of affinity capture assay, immunometric assay, heterogeneous chemiluminescence immunometric assay, homogeneous chemiluminescence immunometric assay, ELISA, western blotting, radioimmunoassay, magnetic immunoassay, real-time immune-quantitative PCR (iqPCR), SERS label free assay and combinations thereof.

4. The method of claim 1, wherein antibodies to one or more of amphiregulin, CCL24, CD69, EGF, HB-EGF, caspase-3, VEGFD, TGF-α, BAFF, CCL9, and/or GH are attached to a solid support, wherein the solid support is a chip, glass slide, a microtiter plate, a bead or resin.

5. The method of claim 4, wherein antibodies to caspase-3, amphiregulin and VEGF-D are attached to the solid support.

* * * * *

UNITED STATES PATENT AND TRADEMARK OFFICE
CERTIFICATE OF CORRECTION

PATENT NO. : 11,946,935 B2
APPLICATION NO. : 17/411524
DATED : April 2, 2024
INVENTOR(S) : Saydam et al.

It is certified that error appears in the above-identified patent and that said Letters Patent is hereby corrected as shown below:

In the Specification

In Column 5, Line 10, delete "NP_116786:" and insert --NP_116786;-- therefor

In Column 15, Table S1-continued, Line 5, delete "06_GIN-15" and insert --06_GDF-15-- therefor In Column 15, Table S1-continued, Line 6, delete "07_PIGF" and insert --07_P1GF-- therefor In Column 15, Table S1-continued, Line 6, delete "56_J-IGF" and insert --56_HGF-- therefor In Column 15, Table S1-continued, Line 14, delete "Dec" and insert --Dcc-- therefor In Column 15, Table S1-continued, Line 21, delete "72_TNTRSF4" and insert --72_TNFRSF4-- therefor In Column 17, Line 48, delete "TGF-a)," and insert --TGF-α),-- therefor In Column 17, Table 1, Line 58, delete "expresso:" and insert --expressed-- therefor In Column 18, Table 1-continued, Line 2, delete "expresso:" and insert --expressed-- therefor In Column 18, Table S2, Line 28, delete "30_1L-2" and insert --30_IL-2-- therefor In Column 23, Line 55, delete "Cararo" and insert --Carraro-- therefor In Column 24, Line 55, delete "Net" and insert --Nel-- therefor In the Claims In Column 31, Line 41, in Claim 1, delete "TGF-a," and insert --TGF-α,-- therefor Signed and Sealed this
Seventh Day of January, 2025

Derrick Brent
*Acting Director of the United States Patent and Trademark Office*

SEQUENCE LISTING

<160> NUMBER OF SEQ ID NOS: 16

<210> SEQ ID NO 1
<211> LENGTH: 19
<212> TYPE: DNA
<213> ORGANISM: Artificial Sequence
<220> FEATURE:
<223> OTHER INFORMATION: A synthetic sequence

<400> SEQUENCE: 1
acatcgctca gacaccatg                                                    19

<210> SEQ ID NO 2
<211> LENGTH: 22
<212> TYPE: DNA
<213> ORGANISM: Artificial Sequence
<220> FEATURE:
<223> OTHER INFORMATION: A synthetic sequence

<400> SEQUENCE: 2
tgtagttgag gtcaatgaag gg                                                22

<210> SEQ ID NO 3
<211> LENGTH: 22
<212> TYPE: DNA
<213> ORGANISM: Artificial Sequence
<220> FEATURE:
<223> OTHER INFORMATION: A synthetic sequence

<400> SEQUENCE: 3
gatctggacc ttttgagagt ca                                                22

<210> SEQ ID NO 4
<211> LENGTH: 22
<212> TYPE: DNA
<213> ORGANISM: Artificial Sequence
<220> FEATURE:
<223> OTHER INFORMATION: A synthetic sequence

<400> SEQUENCE: 4
tgcagaagtc cttgtatttc cg                                                22

<210> SEQ ID NO 5
<211> LENGTH: 20
<212> TYPE: DNA
<213> ORGANISM: Artificial Sequence
<220> FEATURE:
<223> OTHER INFORMATION: A synthetic sequence

<400> SEQUENCE: 5
gctgtcgctc ttgatactcg                                                   20

<210> SEQ ID NO 6
<211> LENGTH: 22
<212> TYPE: DNA
<213> ORGANISM: Artificial Sequence
<220> FEATURE:
<223> OTHER INFORMATION: A synthetic sequence

<400> SEQUENCE: 6
cttcccagag taggtgtcat tg                                                22

<210> SEQ ID NO 7
<211> LENGTH: 20
<212> TYPE: DNA
<213> ORGANISM: Artificial Sequence

```
<220> FEATURE:
<223> OTHER INFORMATION: A synthetic sequence

<400> SEQUENCE: 7
acatggtgct actcttgctg                                          20

<210> SEQ ID NO 8
<211> LENGTH: 21
<212> TYPE: DNA
<213> ORGANISM: Artificial Sequence
<220> FEATURE:
<223> OTHER INFORMATION: A synthetic sequence

<400> SEQUENCE: 8
ctttgccatt tgaccacttc c                                        21

<210> SEQ ID NO 9
<211> LENGTH: 23
<212> TYPE: DNA
<213> ORGANISM: Artificial Sequence
<220> FEATURE:
<223> OTHER INFORMATION: A synthetic sequence

<400> SEQUENCE: 9
aattagtgcc tgttaaagtt gcc                                      23

<210> SEQ ID NO 10
<211> LENGTH: 22
<212> TYPE: DNA
<213> ORGANISM: Artificial Sequence
<220> FEATURE:
<223> OTHER INFORMATION: A synthetic sequence

<400> SEQUENCE: 10
aggacagagt ttcttggaat gg                                       22

<210> SEQ ID NO 11
<211> LENGTH: 18
<212> TYPE: DNA
<213> ORGANISM: Artificial Sequence
<220> FEATURE:
<223> OTHER INFORMATION: A synthetic sequence

<400> SEQUENCE: 11
ttgcaagtgt gaccctgg                                            18

<210> SEQ ID NO 12
<211> LENGTH: 21
<212> TYPE: DNA
<213> ORGANISM: Artificial Sequence
<220> FEATURE:
<223> OTHER INFORMATION: A synthetic sequence

<400> SEQUENCE: 12
tgtagctgaa gtttcccagt g                                        21

<210> SEQ ID NO 13
<211> LENGTH: 20
<212> TYPE: DNA
<213> ORGANISM: Artificial Sequence
<220> FEATURE:
<223> OTHER INFORMATION: A synthetic sequence

<400> SEQUENCE: 13
aaccaaacgg cttctagagg                                          20
```

```
<210> SEQ ID NO 14
<211> LENGTH: 21
<212> TYPE: DNA
<213> ORGANISM: Artificial Sequence
<220> FEATURE:
<223> OTHER INFORMATION: A synthetic sequence

<400> SEQUENCE: 14
ataagcagaa aggcgagact c                                          21

<210> SEQ ID NO 15
<211> LENGTH: 21
<212> TYPE: DNA
<213> ORGANISM: Artificial Sequence
<220> FEATURE:
<223> OTHER INFORMATION: A synthetic sequence

<400> SEQUENCE: 15
acgccatggg acatctaatt c                                          21

<210> SEQ ID NO 16
<211> LENGTH: 20
<212> TYPE: DNA
<213> ORGANISM: Artificial Sequence
<220> FEATURE:
<223> OTHER INFORMATION: A synthetic sequence

<400> SEQUENCE: 16
ttccagtttt gcaatgccag                                            20
```